United States Patent
Matsumoto et al.

(10) Patent No.: US 11,793,414 B2
(45) Date of Patent: Oct. 24, 2023

(54) ELECTRODE UNIT, PULSE WAVE MEASUREMENT UNIT, AND PULSE WAVE MEASUREMENT DEVICE

(71) Applicants: OMRON HEALTHCARE Co., Ltd., Kyoto (JP); OMRON Corporation, Kyoto (JP)

(72) Inventors: Naoki Matsumoto, Kyoto (JP); Naomi Matsumura, Kyoto (JP)

(73) Assignees: OMRON CORPORATION, Kyoto (JP); OMRON HEALTHCARE CO., LTD., Kyoto (JP)

(*) Notice: Subject to any disclaimer, the term of this patent is extended or adjusted under 35 U.S.C. 154(b) by 800 days.

(21) Appl. No.: 16/808,657

(22) Filed: Mar. 4, 2020

(65) Prior Publication Data

US 2020/0196883 A1 Jun. 25, 2020

Related U.S. Application Data

(63) Continuation of application No. PCT/JP2018/030528, filed on Aug. 17, 2018.

(30) Foreign Application Priority Data

Sep. 15, 2017 (JP) ................................. 2017-178080

(51) Int. Cl.
*A61B 5/024* (2006.01)
*A61B 5/0245* (2006.01)
(Continued)

(52) U.S. Cl.
CPC .......... *A61B 5/02444* (2013.01); *A61B 5/022* (2013.01); *A61B 5/0245* (2013.01);
(Continued)

(58) Field of Classification Search
CPC . A61B 5/02444; A61B 5/02108; A61B 5/022; A61B 5/02438; A61B 5/0245;
(Continued)

(56) References Cited

U.S. PATENT DOCUMENTS

| 2008/0221461 A1 | 9/2008 | Zhou et al. | |
| 2010/0076328 A1* | 3/2010 | Matsumura | A61B 5/021 600/500 |

(Continued)

FOREIGN PATENT DOCUMENTS

| CN | 101547634 | 9/2009 |
| CN | 102256542 | 11/2011 |

(Continued)

OTHER PUBLICATIONS

Office Action dated Apr. 6, 2022 in corresponding Chinese Patent Application No. 201880058381.5, with English language translation.

(Continued)

*Primary Examiner* — Erin M Piateski
(74) *Attorney, Agent, or Firm* — Wenderoth, Lind & Ponack, L.L.P.

(57) ABSTRACT

A pulse wave measurement device includes an electrode unit and a pulse wave measurement unit including pairs of current applying electrodes and voltage measuring electrodes. The electrode unit includes a substrate with insulating properties, measurement electrodes, connection electrodes electrically connected to the measurement electrodes in a 1-to-1 manner, and an adhesive layer. The pulse wave measurement unit includes a belt member configured to wrap around a living body and cover the electrode unit attached to a body surface. The pair of current applying electrodes and the pair of voltage measuring electrodes are disposed on an inner circumferential surface of the belt (Continued)

member so that, when the belt member is in a wrapped state around a living body, each one of the pair of current applying electrodes and each one of the pair of voltage measuring electrodes come into contact with any one of the connection electrode.

14 Claims, 29 Drawing Sheets

(51) Int. Cl.
 *A61B 5/00* (2006.01)
 *A61B 5/022* (2006.01)
 *A61B 5/021* (2006.01)
(52) U.S. Cl.
 CPC ...... *A61B 5/02108* (2013.01); *A61B 5/02438* (2013.01); *A61B 5/6831* (2013.01); *A61B 5/6833* (2013.01); A61B 2562/046 (2013.01)
(58) Field of Classification Search
 CPC ................ A61B 5/6831; A61B 5/6833; A61B 2562/046; A61B 5/0295
 See application file for complete search history.

(56) References Cited

U.S. PATENT DOCUMENTS

| 2011/0288393 | A1 | 11/2011 | Holzhacker |
| 2013/0116534 | A1 | 5/2013 | Woo |
| 2013/0331678 | A1 | 12/2013 | Lading et al. |
| 2014/0249434 | A1* | 9/2014 | Banet ................ A61B 5/14551 600/485 |
| 2014/0343392 | A1 | 11/2014 | Yang |
| 2015/0119678 | A1 | 4/2015 | Kato et al. |
| 2016/0242654 | A1 | 8/2016 | Quinlan et al. |
| 2017/0150927 | A1 | 6/2017 | Kubota et al. |
| 2018/0289273 | A1 | 10/2018 | Ariyama et al. |

FOREIGN PATENT DOCUMENTS

| CN | 203234736 | 10/2013 |
| CN | 104545881 | 4/2015 |
| CN | 104771159 | 7/2015 |
| CN | 104812296 | 7/2015 |
| JP | 05-015907 | 3/1993 |
| JP | 05-261073 | 10/1993 |
| JP | H05-261073 A | 10/1993 |
| JP | 2000-333920 | 12/2000 |
| JP | 2000-333920 A | 12/2000 |
| JP | 2004-041482 | 2/2004 |
| JP | 2006-181261 | 7/2006 |
| JP | 2007-44362 | 2/2007 |
| JP | 2008-136655 | 6/2008 |
| JP | 2014-508589 | 4/2014 |
| JP | 2017-047204 | 3/2017 |
| JP | 2017-099619 | 6/2017 |
| JP | 2017-099619 A | 6/2017 |
| KR | 10-2009-0008786 | 1/2009 |
| WO | 2008/065873 | 6/2008 |
| WO | 2008/065873 A1 | 6/2008 |
| WO | 2014/055994 | 4/2014 |
| WO | 2017/013995 | 1/2017 |
| WO | 2017/068751 | 4/2017 |

OTHER PUBLICATIONS

Decision to Grant Patent dated Sep. 7, 2021 in corresponding Japanese Patent Application No. 2017-178080, with English-language translation.
International Search Report dated Sep. 18, 2018 in International (PCT) Application No. PCT/JP2018/030528.
Notice of Grounds of Rejection dated Feb. 16, 2021 in counterpart Japanese Application No. 2017-178080 with English translation.
Office Action dated Jun. 8, 2021 in corresponding Japanese Patent Application No. 2017-178080, with English-language translation.
International Search Report of the International Searching Authority for PCT/JP2018/030528 dated Sep. 18, 2018.
English translation of International Search Report of the International Searching Authority for PCT/JP2018/030528 dated Sep. 18, 2018.
International Preliminary Report on Patentability (Chapter II) of the International Preliminary Examining Authority for PCT/JP2018/030528 dated Jan. 28, 2019.
English translation of International Preliminary Report on Patentability (Chapter II) of the International Preliminary Examining Authority for PCT/JP2018/030528 dated Jan. 28, 2019.
Notification of Granting Patent Right dated Oct. 8, 2022 in corresponding Chinese Patent Application No. 201880058381.5, with English translation.

* cited by examiner

ELECTRODE UNIT, PULSE WAVE MEASUREMENT UNIT, AND PULSE WAVE MEASUREMENT DEVICE

CROSS-REFERENCE TO RELATED APPLICATIONS

This is a continuation of International Application JP 2017-178080 Filed on Sep. 15, 2017 and also PCT/JP2018/030528, with an international filing date of Aug. 17, 2018, filed by applicant, the disclosure of which is hereby incorporated by reference in its entirety.

TECHNICAL FIELD

The present invention relates to an electrode unit, a pulse wave measurement unit, and a pulse wave measurement device used to obtain a volume pulse wave of an artery by measuring a change in bioelectrical impedance.

BACKGROUND ART

An example of a known technology for obtaining a volume pulse wave of an artery using a pulse wave measurement device includes an adhesive sheet attached on a body surface of a living body described in, for example, JP 05-261073 A (Patent Document 1).

In the adhesive sheet disclosed in Patent Document 1, a notch portion is disposed in an intermediate portion of the adhesive sheet in the longitudinal direction, the notch portion extending through the adhesive sheet in the thickness direction and having a size large enough for a pressing surface of a pulse wave sensor including a pressure detection element to pass through. The adhesive sheet is attached to a body surface with the notch portion positioned above a radial artery. In this way, positioning of the pulse wave measurement device is made easier because the pulse wave measurement device can be attached to the body surface of a living body guided by the notch portion.

CITATION LIST

Patent Literature

Patent Document 1: JP 05-261073 A

SUMMARY OF INVENTION

Technical Problem

The adhesive sheet described in Patent Document 1 includes the notch portion and is attached to a body surface positioned above the artery. Thus, in a configuration including a pulse wave sensor in which a plurality of electrodes are brought into contact with the surface of a living body and a change in bioelectrical impedance is measured, because of the thickness of the adhesive sheet and the shape of the electrodes, the electrodes do not fit into the notch portion, making the contact between the electrodes and the body surface of the living body unstable. In this case, measurement precision may decrease.

In a configuration in which an adhesive sheet is not used and a belt member including electrodes is wrapped around a measurement site of the living body, the electrodes are difficult to position above the artery. In this case, one or more of the electrodes may be positioned at a position in the circumferential direction distanced away from above the artery. This may result in a decrease in measurement precision.

The present invention has been made in view of the problems described above, and an object of the present invention is to provide an electrode unit, a pulse wave measurement unit, and a pulse wave measurement device that can perform pulse wave measurement with enhanced measurement precision.

Solution to Problem

A pulse wave measurement device according to an embodiment of the present invention measures a volume pulse wave of an artery by measuring a change in bioelectrical impedance and includes: an electrode unit configured to be attached to a living body; and a pulse wave measurement unit configured to be worn on a living body including a pair of current applying electrodes and a pair of voltage measuring electrodes. The electrode unit includes a substrate with a sheet-like shape and insulating properties including a first main surface and a second main surface, which are front and rear surfaces, measurement electrodes disposed on the first main surface, connection electrodes disposed on the second main surface and electrically connected in a 1-to-1 manner with the measurement electrodes, and an adhesive layer configured to maintain an attached state of the electrode unit being attached to a body surface of a living body. The pulse wave measurement unit includes a belt member configured to wrap around a living body and cover the electrode unit in the attached state. In a case that the belt member is in a wrapped state of being wrapped around a living body covering the electrode unit, the pair of current applying electrodes and the pair of voltage measuring electrodes are disposed on an inner circumferential surface of the belt member, with each one of the pair of current applying electrodes and each one of the pair of voltage measuring electrodes coming into contact with any one of the connection electrodes.

In the pulse wave measurement device according to the embodiment described above of the present invention, preferably, the connection electrodes have a greater size than the measurement electrodes.

In the pulse wave measurement device according to the embodiment described above of the present invention, the measurement electrodes may be arranged side by side in a row. In this case, the connection electrodes may be arranged side by side in a direction parallel to a direction in which the measurement electrodes are arranged.

In the pulse wave measurement device according to the embodiment described above of the present invention, the connection electrodes and the measurement electrodes may be arranged in electrically connected pairs at overlapping positions in a plan view of the substrate.

In the pulse wave measurement device according to the embodiment described above of the present invention, the connection electrodes may be arranged in a matrix-like manner.

In the pulse wave measurement device according to the embodiment described above of the present invention, the electrode unit may further include wire portions that connect the connection electrodes to the measurement electrodes. In this case, the substrate may include a sheet member with insulating properties that includes a front surface and a rear surface, the sheet member being folded with the rear surface facing itself. Also, in this case, the measurement electrodes, the connection electrodes, and the wire portions are preferably formed on the front surface of the sheet member with insulating properties.

In the pulse wave measurement device according to the embodiment described above of the present invention, the belt member includes a length direction corresponding to a circumferential direction of the belt member in the wrapped state and a width direction orthogonal to the length direction. In this case, a width of the pair of current applying electrodes and the pair of voltage measuring electrodes in the width direction is preferably less than a width of the connection electrodes in the width direction.

In the pulse wave measurement device according to the embodiment described above of the present invention, a length of the pair of current applying electrodes and the pair of voltage measuring electrodes in the length direction may be less than a length of the connection electrodes in the length direction.

In the pulse wave measurement device according to the embodiment described above of the present invention, the connection electrodes may be arranged in a matrix-like manner. In this case, the pair of current applying electrodes and the pair of voltage measuring electrodes may be arranged in a matrix-like manner.

In the pulse wave measurement device according to the embodiment described above of the present invention, the belt member includes a length direction corresponding to a circumferential direction of the belt member in the wrapped state. In this case, a length of the pair of current applying electrodes and the pair of voltage measuring electrodes in the length direction may be greater than a length of the connection electrodes in the length direction.

An electrode unit according to an embodiment of the present invention is used to measure a volume pulse wave of an artery by measuring a change in bioelectrical impedance and includes:

a substrate with a sheet-like shape and insulating properties including a first main surface and a second main surface, which are front and rear surfaces;

measurement electrodes disposed on the first main surface;

connection electrodes disposed on the second main surface; and an adhesive layer configured to maintain an attached state of the electrode unit being attached to a body surface of a living body. The connection electrodes and the measurement electrodes are electrically connected in a 1-to-1 manner.

In the electrode unit according to the embodiment described above of the present invention, preferably, the connection electrodes have a greater size than the measurement electrodes.

In the electrode unit according to the embodiment described above of the present invention, the measurement electrodes may be arranged side by side in a row. In this case, the connection electrodes may be arranged side by side in a direction parallel to a direction in which the measurement electrodes are arranged.

In the electrode unit according to the embodiment described above of the present invention, the connection electrodes and the measurement electrodes may be arranged in electrically connected pairs at overlapping positions in a plan view of the substrate.

In the electrode unit according to the embodiment described above of the present invention, the connection electrodes may be arranged in a matrix-like manner.

In the electrode unit according to the embodiment described above of the present invention, the electrode unit may further include wire portions that connect the connection electrodes to the measurement electrodes. In this case, the substrate may include a sheet member with insulating properties that includes a front surface and a rear surface, the sheet member being folded with the rear surface facing itself. Also, in this case, the measurement electrodes, the connection electrodes, and the wire portions are preferably formed on the front surface of the sheet member with insulating properties.

A pulse wave measurement unit according to an embodiment of the present invention is configured to be worn on a living body for measuring a volume pulse wave of an artery by measuring a change in bioelectrical impedance and includes:

a pair of current applying electrodes and a pair of voltage measuring electrodes; and a belt member configured to wrap around a living body and cover an electrode unit in a state in which the electrode unit is attached to a body surface of a living body, the electrode unit being configured to be attached to a body surface of a living body and including measurement electrodes and connection electrodes disposed on front and rear surfaces of a sheet-like substrate with insulating properties electrically connected in a 1-to-1 manner. In a case that the belt member is in a wrapped state of being wrapped around a living body covering the electrode unit, the pair of current applying electrodes and the pair of voltage measuring electrodes are disposed on an inner circumferential surface of the belt member, with each one of the pair of current applying electrodes and each one of the pair of voltage measuring electrodes coming into contact with any one of the connection electrodes.

In the pulse wave measurement unit according to the embodiment described above of the present invention, the belt member includes a length direction corresponding to a circumferential direction of the belt member in the wrapped state and a width direction orthogonal to the length direction. In this case, the pair of current applying electrodes and the pair of voltage measuring electrodes may be arranged side by side in the width direction.

In the pulse wave measurement unit according to the embodiment described above of the present invention, the pair of current applying electrodes and the pair of voltage measuring electrodes may extend from one end of the belt member in the length direction to another end.

In the pulse wave measurement unit according to the embodiment described above of the present invention, the pair of current applying electrodes and the pair of voltage measuring electrodes may be arranged in a matrix-like manner.

Advantageous Effects of Invention

According to the present invention, an electrode unit, a pulse wave measurement unit, and a pulse wave measurement device that can perform pulse wave measurement with enhanced measurement precision can be provided.

DESCRIPTION OF EMBODIMENTS

Figure 1:
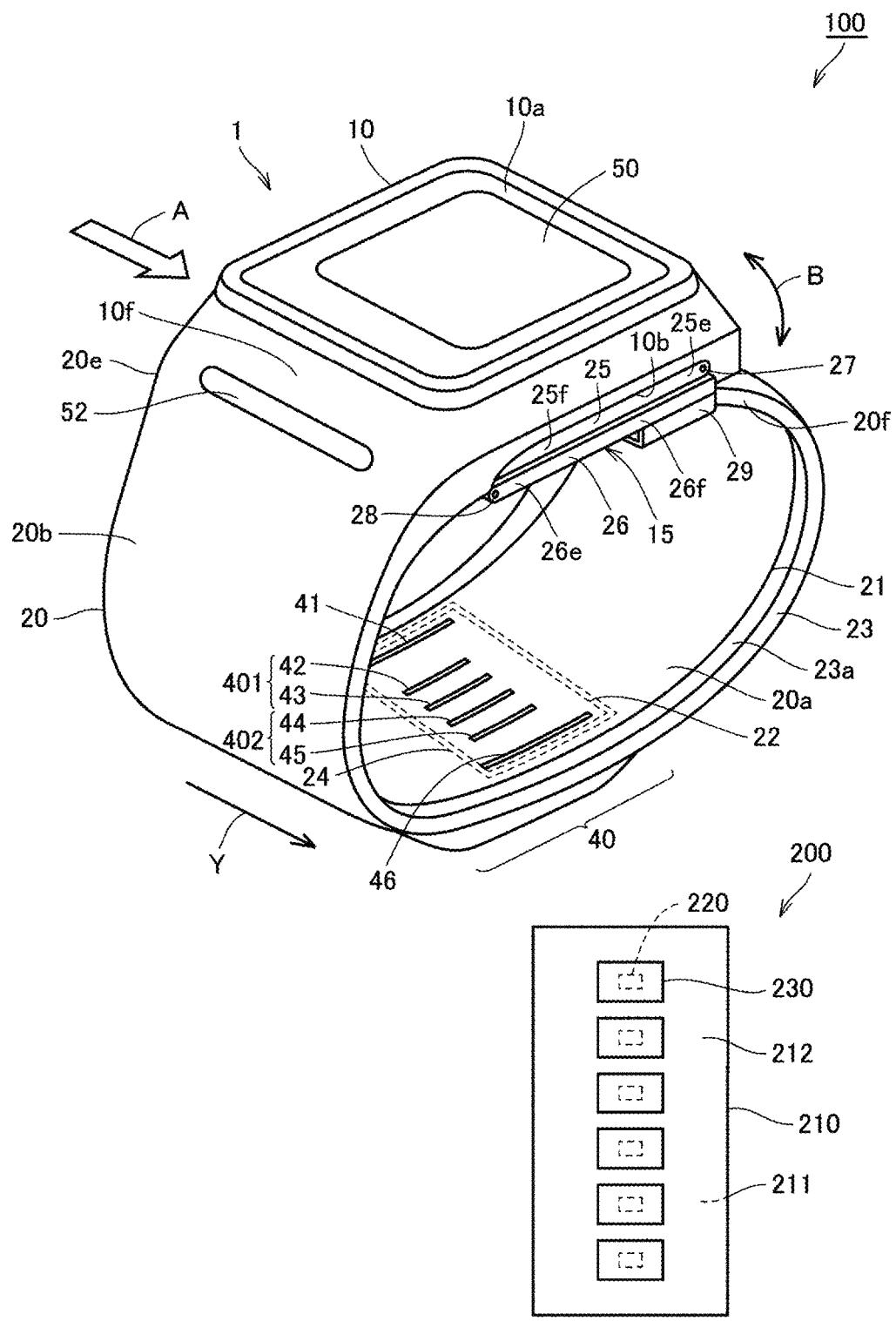
FIG. 1 is a perspective view illustrating a pulse wave measurement device according to a first embodiment.

Embodiments of the present invention will be described in detail below with reference to the drawings. Note that in the following embodiments, identical or common components are given the same reference signs in the drawings, and the descriptions thereof are not repeated.

First Embodiment

FIG. 1 is a perspective view illustrating a pulse wave measurement device according to a first embodiment. A pulse wave measurement device 100 according to the first embodiment will be described with reference to FIG. 1.

The pulse wave measurement device 100 illustrated in FIG. 1 measures a volume pulse wave of an artery by measuring a change in bioelectrical impedance. The pulse wave measurement device 100 includes a pulse wave measurement unit 1 and an electrode unit 200.

Figure 2:
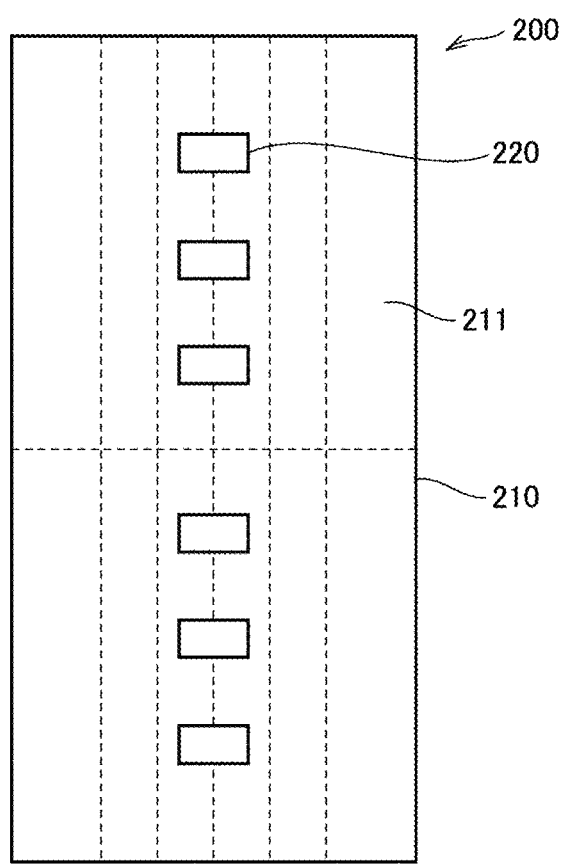
FIG. 2 is a plan view illustrating a first main surface side of the electrode unit according to the first embodiment.
Figure 3:
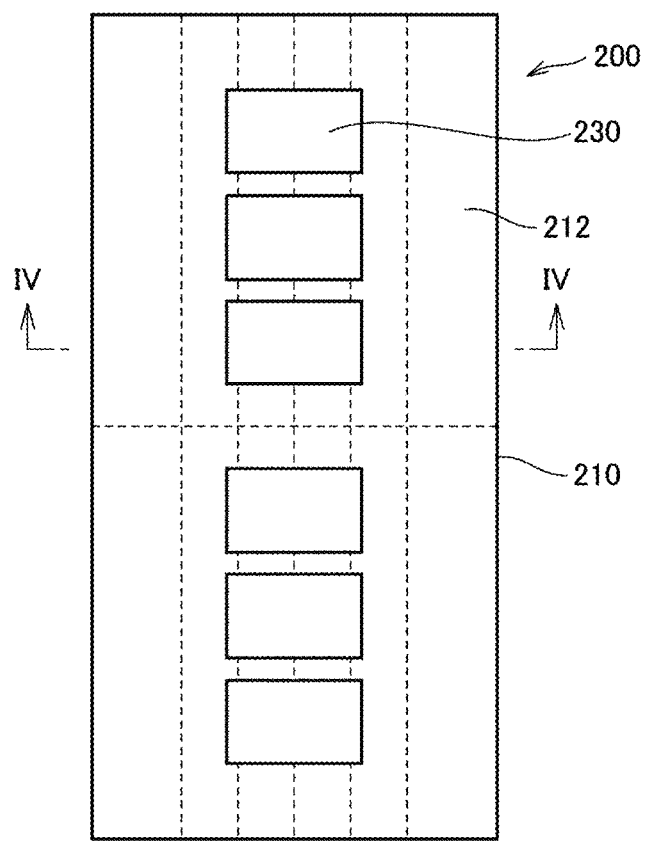
FIG. 3 is a plan view illustrating a second main surface side of the electrode unit according to the first embodiment.
Figure 4:
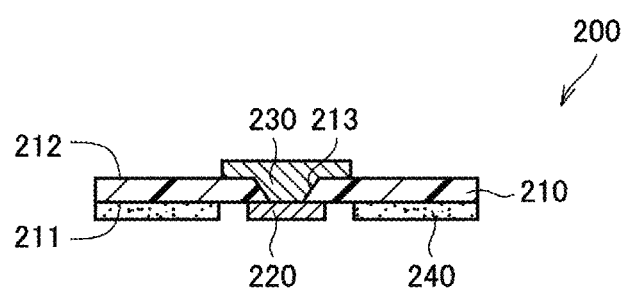
FIG. 4 is a cross-sectional view taken along line IV-IV illustrated in FIG. 3.

FIG. 2 is a plan view illustrating a first main surface side of the electrode unit according to the first embodiment. FIG. 3 is a plan view illustrating a second main surface side of the electrode unit according to the first embodiment. FIG. 4 is a cross-sectional view taken along line IV-IV illustrated in FIG. 3. The electrode unit 200 according to the first embodiment will be described with reference to FIGS. 2 to 4.

The electrode unit 200 illustrated in FIGS. 2 to 4 are used to measure a volume pulse wave of an artery by measuring a change in bioelectrical impedance. The electrode unit 200 is configured to be attach to a living body.

The electrode unit 200 includes a substrate 210 with a sheet-like shape and insulating properties, a plurality of measurement electrodes 220, a plurality of connection electrodes 230, and an adhesive layer 240.

The substrate 210 includes a first main surface 211 and a second main surface 212 which are front and rear surfaces. The substrate 210 has a substantially rectangular shape and includes a film with insulating properties. The substrate 210 preferably has flexibility so that it can conform to the uneven form of the body surface of a living body.

The thickness of the substrate 210 is approximately 0.2 mm. The external dimensions of the substrate 210 are approximately 5 mm×2 mm.

Examples of materials that can be used for the substrate 210 include insulating resin materials, such as polyvinyl chloride, polyethylene, polyester, epoxy, polyurethane, and polyimide. Note that the substrate 210 may be made of a nonwoven fabric.

The measurement electrodes 220 are disposed on the first main surface 211. The measurement electrodes 220 are arranged side by side in a row. The number of measurement electrodes 220 depends on the number of electrodes 41 to 46 described below of the pulse wave measurement unit 1. The measurement electrodes 220 come into contact with the body surface of a living body when the electrode unit 200 is attached to the body surface of a living body, i.e., in an attached state.

The connection electrodes 230 are disposed on the second main surface 212. The connection electrodes 230 are electrically connected with the measurement electrodes 220 in a 1-to-1 manner. The connection electrodes 230 are arranged side by side in a row. The connection electrodes 230 are arranged side by side in the direction parallel with the direction in which the measurement electrodes 220 are arranged.

The connection electrodes 230 overlap the measurement electrodes 220 when viewed in the direction in which the first main surface 211 and the second main surface 212 overlap. In other words, the connection electrodes 230 and the measurement electrodes 220 are arranged in electrically connected pairs at overlapping positions in a plan view of the substrate 210. The size of the connection electrodes 230 is greater than the size of the measurement electrodes 220.

The adhesive layer 240 maintains the attached state of the electrode unit 200 being attached to the body surface of a living body. The adhesive layer 240 is disposed on the first main surface 211 with the measurement electrodes 220 exposed. Examples of materials that can be used for the adhesive layer 240 include a rubber-based adhesive, an acrylic-based adhesive, a silicone-based adhesive, and a urethane-based adhesive. The material of the adhesive layer 240 is preferably a material that can be in contact with the surface of a living body for an extended period of time and not cause irritation such as a rash, and preferably a material that causes minimal damage to body tissue when the electrode unit 200 is removed from the body surface.

Note that the adhesive layer 240 may be disposed on the measurement electrodes 220 instead of being disposed on the first main surface 211. In this case, the adhesive layer 240 includes conductive particles and has conductivity.

Figure 5:
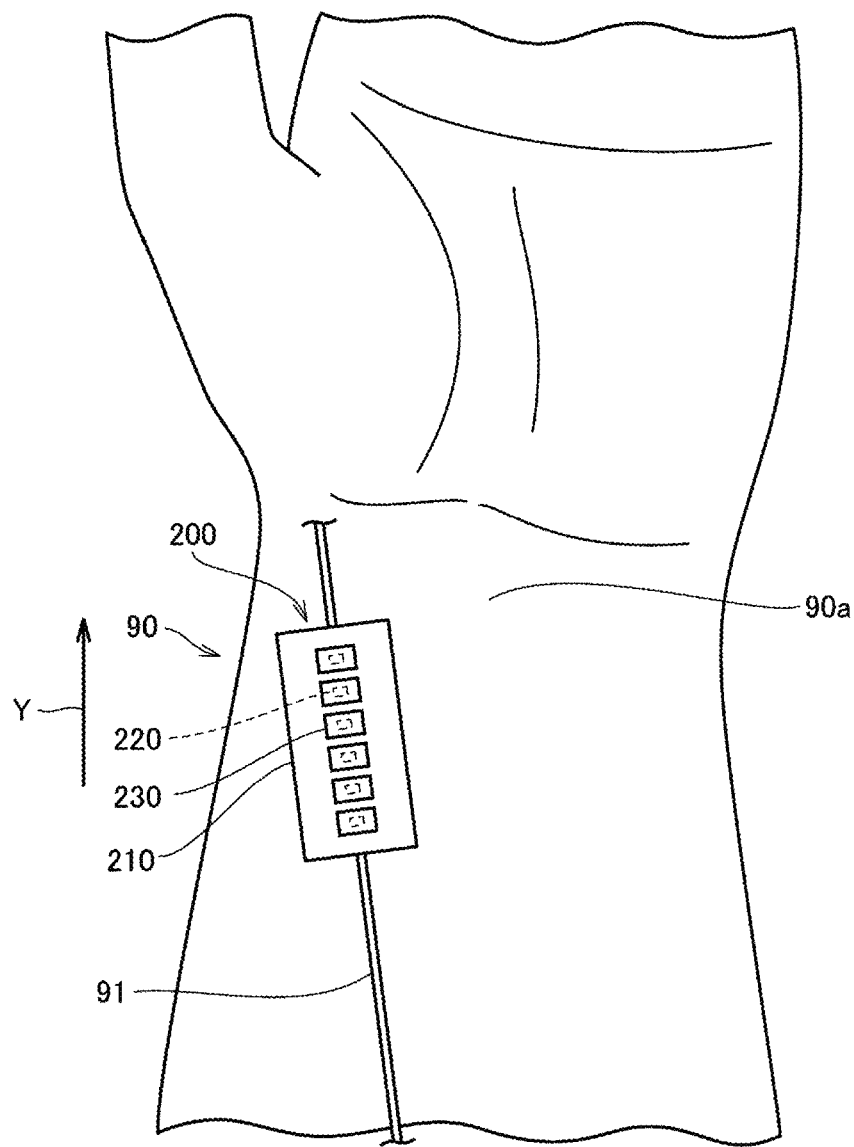
FIG. 5 is a diagram illustrating the electrode unit according to the first embodiment attached to the left wrist.

FIG. 5 is a diagram illustrating the electrode unit according to the first embodiment attached to the left wrist. The electrode unit 200 will be described in the state of being attached to a left wrist 90 with reference of FIG. 5.

As illustrated in FIG. 5, the electrode unit 200 is attached to the left wrist 90 with the measurement electrodes 220 positioned above a radial artery 91. In the attached state of the electrode unit 200 being attached to the left wrist 90, the measurement electrodes 220 are arranged side by side in the direction in which the radial artery 91 extends.

Figure 6:
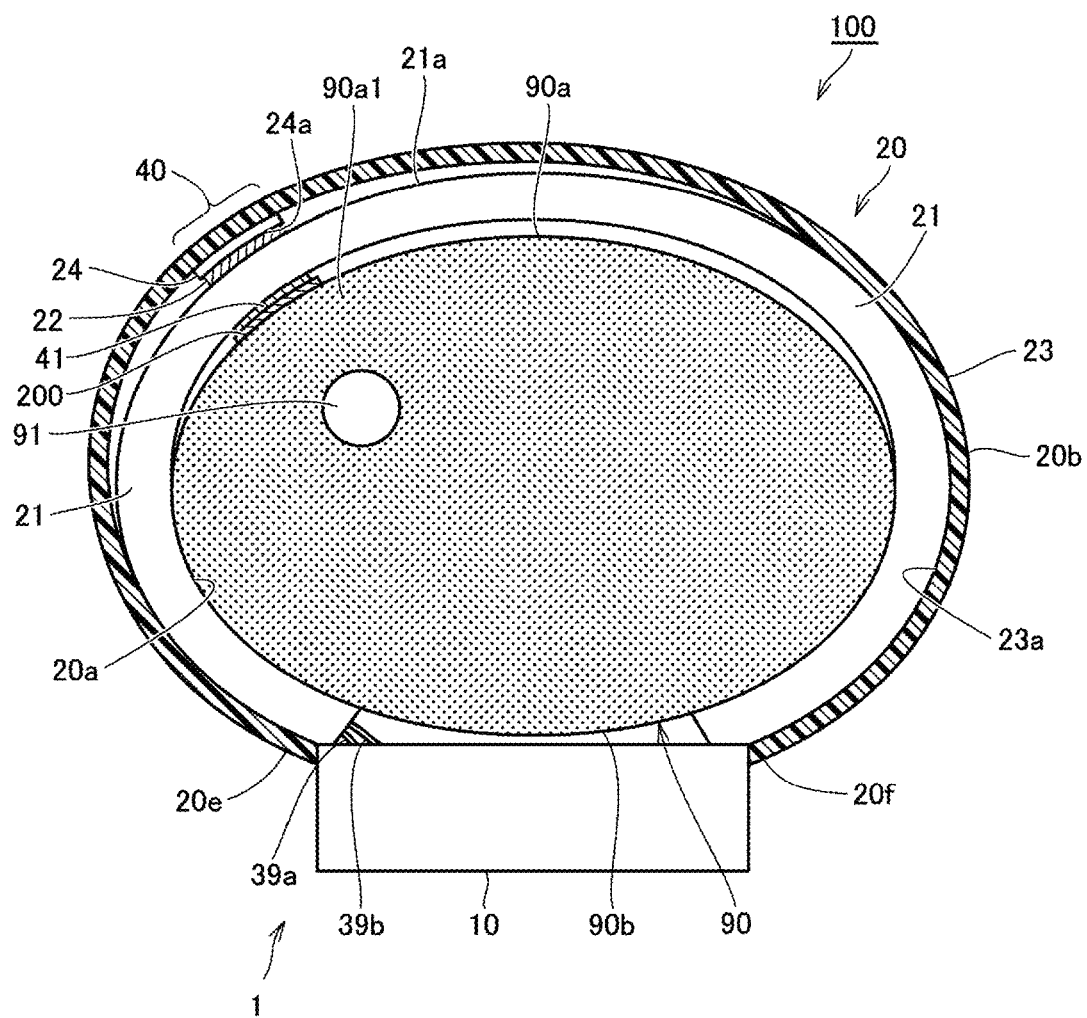
FIG. 6 is a diagram schematically illustrating the pulse wave measurement device according to the first embodiment in a cross-section perpendicular to the longitudinal direction of the wrist, the pulse wave measurement device being worn on the left wrist.

FIG. 6 is a diagram schematically illustrating the pulse wave measurement device according to the first embodiment in a cross-section perpendicular to the longitudinal direction of the wrist, the pulse wave measurement device being worn on the left wrist. The pulse wave measurement unit 1 will be described with reference to FIGS. 1 and 6.

As illustrated in FIGS. 1 and 6, the pulse wave measurement unit 1 is configured to be attached to a living body and to measure a volume pulse wave of an artery by measuring a change in bioelectrical impedance.

The pulse wave measurement unit 1 includes a belt (belt member) 20, the electrodes 41 to 46 including a pair of current applying electrodes and a pair of voltage measuring electrodes, and a body 10 integrally formed with the belt 20.

The belt 20 is configured to be attached to the body surface of a living body and configured to wrap around a living body covering the electrode unit 200, with the electrode unit 200 including the measurement electrodes 220 and the connection electrodes 230 on the front and rear surfaces of the substrate 210 with insulating properties being attached to the body surface of a living body.

The belt 20 has an elongated band-like shape allowing it to wrap around the left wrist 90 in the circumferential direction. The dimension (width dimension) of the belt 20 in a width direction Y is, for example, approximately 30 mm. The belt 20 includes a band 23 that constitutes an outer circumferential surface 20*b* and a compression cuff 21 attached and conforming to an inner circumferential surface 23*a* of the band 23. The compression cuff 21 is a fluid bag that constitutes an inner circumferential surface 20*a* that comes into contact with the left wrist 90. The compression cuff 21, like the belt 20, has an elongated band-like shape allowing it to wrap around the left wrist 90 in the circumferential direction.

The body 10 is integrally formed with the belt 20 at one end portion 20*e* in the circumferential direction via integral forming, for example. Note that the belt 20 and the body 10 may be formed separately, and the body 10 may be integrally attached to the belt 20 using an engagement member such as a hinge.

The portion where the body 10 is disposed corresponds to a back side surface (surface on the back side of the hand) 90*b* (see FIG. 6) of the left wrist 90 when the device is worn. A radial artery 91 runs through the left wrist 90 near a palm side surface (surface on the palm side of the hand) 90*a* (see FIG. 6).

Returning to FIG. 1, the body 10 has a thickness in the direction perpendicular to the outer circumferential surface 20*b* of the belt 20. The body 10 is formed compact and thin, so as to not interfere with the daily activities of the user. The body 10 has a truncated quadrangular pyramid profile protruding outward from the belt 20.

A display 50 including a display screen is provided on a top surface (surface on the far side from the target measurement site) 10*a* of the body 10. Also, an operation portion 52 is provided along a side surface (side surface on the left front side in FIG. 1) 10*f* of the body 10. The operation portion 52 is for the input of instructions from the user.

The belt 20 is provided with the electrodes 41 to 46 on the inner circumferential surface 20*a* of the compression cuff 21, which constitutes the inner circumferential surface 20*a* of the belt 20, at a portion in the circumferential direction between a first end portion 20*e* and a second end portion 20*f*.

The six electrodes 41 to 46 are separated from one another in a width direction Y of the belt 20. The electrodes 41 to 46 each have a plate-like shape. Of the electrodes 41 to 46, the electrodes 41 and 46 are a pair of current applying electrodes. Of the electrodes 41 to 46, the electrodes 42 and 43 are a pair of voltage measuring electrodes. Of the electrodes 41 to 46, the electrodes 44 and 45 are another pair of voltage measuring electrodes.

When the belt 20 is in a wrapped state of being wrapped around the living body covering the electrode unit 200, the electrodes 41 to 46 are disposed on the inner circumferential surface 20a of the belt 20, in a manner such that each of the electrodes 41 to 46 including the pair of current applying electrodes and the pairs of voltage measuring electrodes comes into contact with any one of the connection electrodes 230. In this wrapped state, each of the electrodes 41 to 46 including the pair of current applying electrode and the pairs of voltage measuring electrodes comes into contact with a different connection electrode 230.

The electrodes 42, 43 function as a first pulse wave sensor 401. The electrodes 44, 45 function as a second pulse wave sensor 402. The first pulse wave sensor 401 and the second pulse wave sensor 402 are disposed between the electrodes 41, 46. The second pulse wave sensor 402 is disposed between the first pulse wave sensor 401 and the electrode 46. The first pulse wave sensor 401, the second pulse wave sensor 402, and a circuit board including a current flow and voltage detection circuit 49 described below (see FIG. 8) constitute an impedance measurement portion 40.

A distance D (see FIG. 9) in the width direction Y between a central point between the electrodes 42, 43 and a central point between the electrodes 44, 45 is approximately 20 mm, for example. The distance D corresponds to the actual interval between the first pulse wave sensor 401 and the second pulse wave sensor 402. For example, the interval in the width direction Y between the electrodes 42, 43 is approximately 2 mm, and the interval in the width direction Y between the electrodes 44, 45 is approximately 2 mm.

The electrodes 41 to 46 can have a flat configuration. Thus, the belt 20 of the pulse wave measurement unit 1 can have an overall thin configuration. Also, the electrodes 41 to 46 can have a flexible configuration. Thus, the electrodes 41 to 46 do not interfere with the compression of the left wrist 90 by the compression cuff 21, preventing a decrease in the precision of the blood pressure measurement performed via the oscillometric method described below.

A solid material 22 is disposed on an outer circumferential surface 21a that is on the opposite side of the inner circumferential surface 20a of the compression cuff 21 where the electrodes 41 to 46 is disposed. The solid material 22 is disposed at a position corresponding to the electrodes 41 to 46. Also, a pressing cuff 24 is disposed on the outer circumference side of the solid material 22. The pressing cuff 22 is an expandable member that locally presses against a region in the circumferential direction of the compression cuff 21 corresponding to the electrodes 41 to 46.

The pressing cuff 24 is disposed on the inner circumferential surface 23a of the band 23 constituting the belt 20. The pressing cuff 24 is a fluid bag that expands and contracts in the thickness direction of the belt 20. The pressing cuff 24 is formed by welding together edge portions of two stretchable polyurethane sheets layered in the thickness direction. The pressing cuff 24 is put in a pressurized state when fluid is supplied and in a non-pressurized state when fluid is discharged.

As illustrated in FIG. 1, a bottom surface (surface on the near side to the target measurement site) 10b of the body 10 and the end portion 20f of the belt 20 are connected via a tri-fold buckle 15. The buckle 15 includes a first plate-like member 25 disposed on the outer circumference side and a second plate-like member 26 disposed on the inner circumference side.

A first end portion 25e of the first plate-like member 25 is attached in a freely rotatable manner to the body 10 via a connecting rod 27 that extends in the width direction Y. A second end portion 25f of the first plate-like member 25 is attached in a freely rotatable manner to a first end portion 26e of the second plate-like member 26 via a connecting rod 28 that extends in the width direction Y. A second end portion 26f of the second plate-like member 26 is fixed at a position near the end portion 20f of the belt 20 via a fixing portion 29.

Note that the attachment position of the fixing portion 29 in the circumferential direction of the belt 20 is set in advance in accordance with the circumference length of the left wrist 90 of the user. Thus, the pulse wave measurement unit 1 (belt 20) is formed in an overall substantially annular shape, and the buckle 15 can open and close in the arrow B direction to separate and bring together the bottom surface 10b of the body 10 and the end portion 20f of the belt 20.

As illustrated in FIG. 6, the band 23 has flexibility in the thickness direction and is made of a plastic material that is substantially non-stretchable in the circumferential direction (longitudinal direction). The compression cuff 21 is formed by, for example, welding together edge portions of two stretchable polyurethane sheets layered in the thickness direction.

As illustrated in FIG. 1, when the pulse wave measurement unit 1 is worn on the left wrist 90, the buckle 15 is opened to increase the annular diameter of the belt 20 and the user puts their left hand through the belt 20 in the arrow A direction illustrated in FIG. 1. Before the pulse wave measurement unit 1 is worn, the electrode unit 200 is attached to the left wrist 90 in advance as illustrated in FIG. 5.

Then, as illustrated in FIG. 6, the belt 20 is disposed covering the attached electrode unit 200. Next, the user adjusts the position of the belt 20 in the width direction and the angular position of the belt 20 around the left wrist 90, making each of the electrodes 41 to 46 come into contact with any one of the connection electrodes 230. In this state, the buckle 15 is closed. This wraps the belt 20 around the living body with each of the electrodes 41 to 46 in contact with any one of the connection electrodes 230. In this way, the pulse wave measurement device 100 is worn on the living body.

Figure 7:
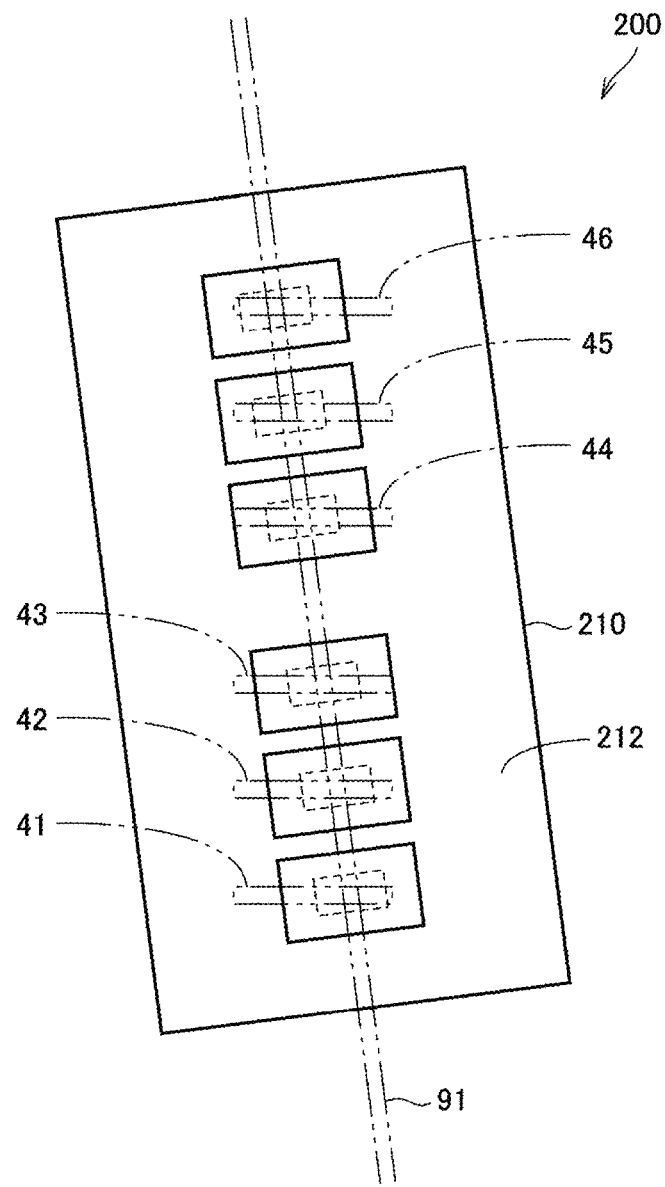
FIG. 7 is a plan view illustrating the positional relationship between the radial artery, measurement electrodes and connection electrodes of the electrode unit, and electrodes of a pulse wave measurement unit, when the pulse wave measurement device according to the first embodiment is worn on the left wrist.

FIG. 7 is a plan view illustrating the positional relationship between the radial artery, the measurement electrodes and the connection electrodes of the electrode unit, and the electrodes of the pulse wave measurement unit, when the pulse wave measurement device according to the first embodiment is worn on the left wrist. Note that FIG. 7 is a plan view of the second main surface 212 side of the electrode unit 200 in an attached state. The radial artery 91 and the electrodes 41 to 46 overlap one another in the plan view and are illustrated with a two-dot chain line.

As illustrated in FIG. 7, with the pulse wave measurement device 100 in a worn state, the measurement electrodes 220 are arranged above the radial artery 91 running through the left wrist 90. Each of the electrodes 41 to 46 is in contact with any one of the connection electrodes 230. Each of the electrodes 41 to 46 is in contact with a different one of the connection electrodes 230. Accordingly, the electrodes 41 to 46 are electrically connected, via the connection electrodes 230, to the measurement electrodes 220 which are electrically connected in a 1-to-1 manner to the connection electrodes 230.

The width of the electrodes 41 to 46 in the width direction of the belt 20 is less than the width of the connection electrodes 230 in the width direction. Thus, this can minimize or prevent contact between a portion of an electrode of the electrodes 41 to 46 not overlapping with one connection electrode 230 in contact with the electrode and other connection electrodes 230.

The length of the electrodes 41 to 46 in the length direction of the belt 20 is greater than the length of the connection electrodes 230 in the length direction. Thus, in a plan view of the substrate 210, in the case where the width direction of the belt 20 in a wrapped state and the direction in which the connection electrodes 230 are arranged intersect, at least one of the electrodes 41 to 46 can easily come into contact with one of the connection electrodes 230. This allows the pulse wave measurement unit 1 to be easily worn on a living body.

Figure 8:
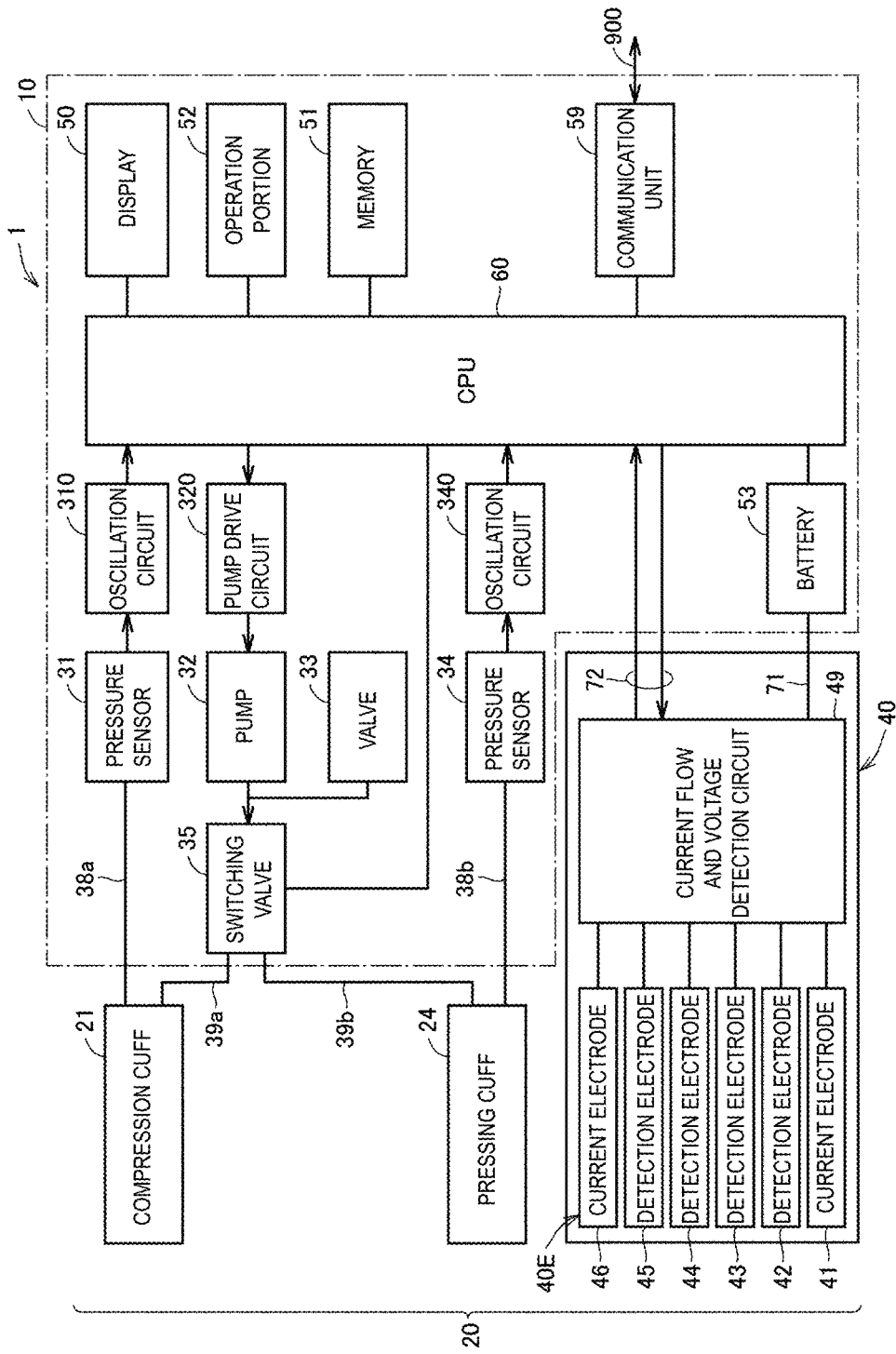
FIG. 8 is a block diagram illustrating the control configuration of the pulse wave measurement unit according to the first embodiment.

FIG. 8 is a block diagram illustrating the control configuration of the pulse wave measurement unit according to the first embodiment. The control configuration of the pulse wave measurement unit 1 will be described with reference to FIG. 8.

As illustrated in FIG. 8, the display 50 and the operation portion 52 described above and a CPU 60, i.e., a control unit, a memory 51, i.e., a storage unit, and a communication unit 59 are disposed in the body 10 of the pulse wave measurement unit 1. Also, a first pressure sensor 31, a pump 32, i.e., a fluid supply source, a valve 33, and a second pressure sensor 34 are disposed in the body 10. Also, an oscillation circuit 310 and an oscillation circuit 340 that convert the output of the first pressure sensor 31 and the second pressure sensor 34, respectively, into a frequency and a pump drive circuit 320 that drives the pump 32 are disposed in the body 10. Also, the electrodes 41 to 46 and the current flow and voltage detection circuit 49 are disposed in the impedance measurement portion 40. Also, a switching valve 35 for switching the connection destination of the pump 32 and the valve 33 between the compression cuff 21 and the pressing cuff 24 is provided.

The display 50 includes an organic EL display, for example. The display 50 displays information relating to blood pressure measurement such as blood pressure measurement results and other information in accordance with a control signal from the CPU 60. Note that the display 50 is not limited to being an organic EL display and may be another type of display such as a liquid crystal display.

The operation portion 52 includes, for example, a push type switch and inputs to the CPU 60 an operation signal in response to an instruction from the user to start or stop blood pressure measurement. Note that the operation portion 52 is not limited to being a push type switch and may be, for example, a pressure sensitive type (resistance type) or a proximity type (capacitance type) touch panel type switch. Also, a microphone (not illustrated) may be provided for input of a start blood pressure measurement instruction from the user via sound.

The memory 51 non-transitorily stores data of a program for controlling the pulse wave measurement unit 1, data used to control the pulse wave measurement unit 1, settings data for setting various functions of the pulse wave measurement unit 1, data of measurement results of blood pressure values, and the like. Also, the memory 51 is used as working memory and the like for executing a program.

The CPU 60 executes various functions as a control unit in accordance with a program for controlling the pulse wave measurement unit 1 stored in the memory 51. For example, in the case where blood pressure measurement is executed via the oscillometric method, the CPU 60 drives the pump 32 (and the valve 33) in accordance with a blood pressure measurement start instruction from the operation portion 52 on the basis of a signal from the first pressure sensor 31. Also, the CPU 60 calculates the blood pressure value on the basis of a signal from the first pressure sensor 31, for example.

In the case where blood pressure measurement (estimation) based on pulse transit time is executed, the CPU 60 drives the valve 33 so that air inside the compression cuff 21 is discharged in accordance with a blood pressure measurement start instruction from the operation portion 52. Also, the CPU 60 drives the switching valve 35 and switches the connection destination of the pump 32 (and the valve 33) to the pressing cuff 24. Furthermore, the CPU 60 calculates the blood pressure value on the basis of a signal from the second pressure sensor 34.

The communication unit 59 is controlled by the CPU 60, sends predetermined information to an external device via a network 900 and receives information from an external device via the network 900, and relays the information to the CPU 60. The communication via the network 900 may be wireless or wired. In the present embodiment, the network 900 is the Internet (trade name), but it is not limited thereto. The network 900 may be another network such as an intra-hospital LAN or a one-to-one communication using a USB cable or the like. The communication unit 59 may include a USB connector.

The pump 32 and the valve 33 are connected to the compression cuff 21 and the pressing cuff 24 via the switching valve 35 and air lines 39a, 39b. Also, the first pressure sensor 31 is connected to the compression cuff 21 via an air line 38a. The first pressure sensor 31 detects the pressure in the compression cuff 21. The second pressure sensor 34 is connected to the pressing cuff 24 via an air line 38b. The second pressure sensor 34 detects the pressure in the pressing cuff 24.

The switching valve 35 is driven in accordance with a control signal from the CPU 60 and switches the connection destination of the pump 32 and the valve 33 between the compression cuff 21 and the pressing cuff 24. The pump 32 includes a piezoelectric pump, for example. In the case where the connection destination of the pump 32 and the valve 33 is switched to the compression cuff 21 by the switching valve 35, the pump 32 supplies air, i.e., pressurization fluid, into the compression cuff 21 via the air line 39a. This pressurizes the inside of the compression cuff 21. In the case where the connection destination of the pump 32 and the valve 33 is switched to the pressing cuff 24 by the switching valve 35, the pump 32 supplies air, i.e., pressurization fluid, into the pressing cuff 24 via the air line 39b. This pressurizes the inside of the pressing cuff 24.

The pump 32 is provided with the valve 33, and the valve 33 is configured to be controlled to be opened and closed in accordance with the pump 32 being on and off.

When the connection destination of the pump 32 and the valve 33 is switched to the compression cuff 21 via the switching valve 35 and the pump 32 is turned on, the valve 33 closes. This allows air to be supplied inside the compression cuff 21. When the pump 32 is turned off, the valve 33 opens. This allows the air inside the compression cuff 21 to discharge out into the atmosphere via the air line 39a.

When the connection destination of the pump 32 and the valve 33 is switched to the pressing cuff 24 via the switching valve 35 and the pump 32 is turned on, the valve 33 closes. This allows air to be supplied inside the pressing cuff 24. When the pump 32 is turned off, the valve 33 opens. This allows the air inside the pressing cuff 24 to discharge out into the atmosphere via the air line 39b.

Note that, the valve 33 functions as a check valve, preventing the discharged air from flowing in reverse. The pump drive circuit 320 drives the pump 32 on the basis of a control signal from the CPU 60.

As the first pressure sensor 31, a piezoresistive pressure sensor can be used, for example. The first pressure sensor 31 is connected to the pump 32, the valve 33, and the compression cuff 21 via an air line 38a. The first pressure sensor 31 detects the pressure of the belt 20 (compression cuff 21) via the air line 38a and outputs a time series signal. Note that the pressure is detected using atmospheric pressure as a reference (zero).

The oscillation circuit 310 produces an oscillating electrical signal on the basis of the change in electric resistance of the first pressure sensor 31 due to the piezoresistive effect. In this way, the oscillation circuit 310 outputs to the CPU 60 a frequency signal having a frequency corresponding to the electrical signal value of the first pressure sensor 31. For example, the output of the first pressure sensor 31 is used to control the pressure of the compression cuff 21 and to calculate blood pressure values (including for systolic blood pressure and for diastolic blood pressure) via the oscillometric method.

In the case where blood pressure is measured in accordance with a typical oscillometric method, generally, the following occurs. Prior to measurement, the cuff is wrapped around the target measurement site (arm or the like) of the subject. In the measurement, the CPU 60 controls the pump 32 and the valve 33 to increase the cuff pressure above the systolic blood pressure, and then gradually decreases the cuff pressure. In the reducing pressure process, the cuff pressure is detected by the pressure sensor, and the variation of arterial volume generated in the artery at the target measurement site is determined to be a pulse wave signal. The systolic blood pressure and diastolic blood pressure are calculated on the basis of the change in amplitude of the pulse wave signal corresponding to the change in the cuff pressure at the time (mainly, a rising edge and a falling edge).

As the second pressure sensor 34, a piezoresistive pressure sensor can be used, for example. The second pressure sensor 34 is connected to the pump 32, the valve 33, and the pressing cuff 24 via an air line 38b. The second pressure sensor 34 detects the pressure of the pressing cuff 24 via the air line 38b and outputs a time series signal. Note that the pressure is detected using atmospheric pressure as a reference (zero).

The oscillation circuit 340 produces an oscillating electrical signal on the basis of the change in electric resistance in the second pressure sensor 34 due to the piezoresistive effect. In this way, the oscillation circuit 340 outputs to the CPU 60 a frequency signal having a frequency corresponding to the electrical signal value of the second pressure sensor 34. For example, the output of the second pressure sensor 34 is used to control the pressure of the pressing cuff 24 and to calculate the blood pressure on the basis of pulse transit time. When the pressure of the pressing cuff 24 is controlled to measure the blood pressure based on pulse transit time, the CPU 60 controls the pump 32 and the valve 33 and increases and reduces the pressure, i.e., cuff pressure, in accordance with various conditions.

A battery 53 supplies power to the components disposed in the body 10 including, in the present embodiment, the CPU 60, the first pressure sensor 31, the pump 32, the valve 33, the display 50, the memory 51, the communication unit 59, the oscillation circuit 310, and the pump drive circuit 320. Also, the battery 53 supplies power to the current flow and voltage detection circuit 49 of the impedance measurement portion 40 via a wire 71. The wire 71 is disposed together with a wire 72 for signals between the band 23 and the compression cuff 21 of the belt 20 and extends in the circumferential direction of the belt 20 between the body 10 and the impedance measurement portion 40.

Figure 9A:
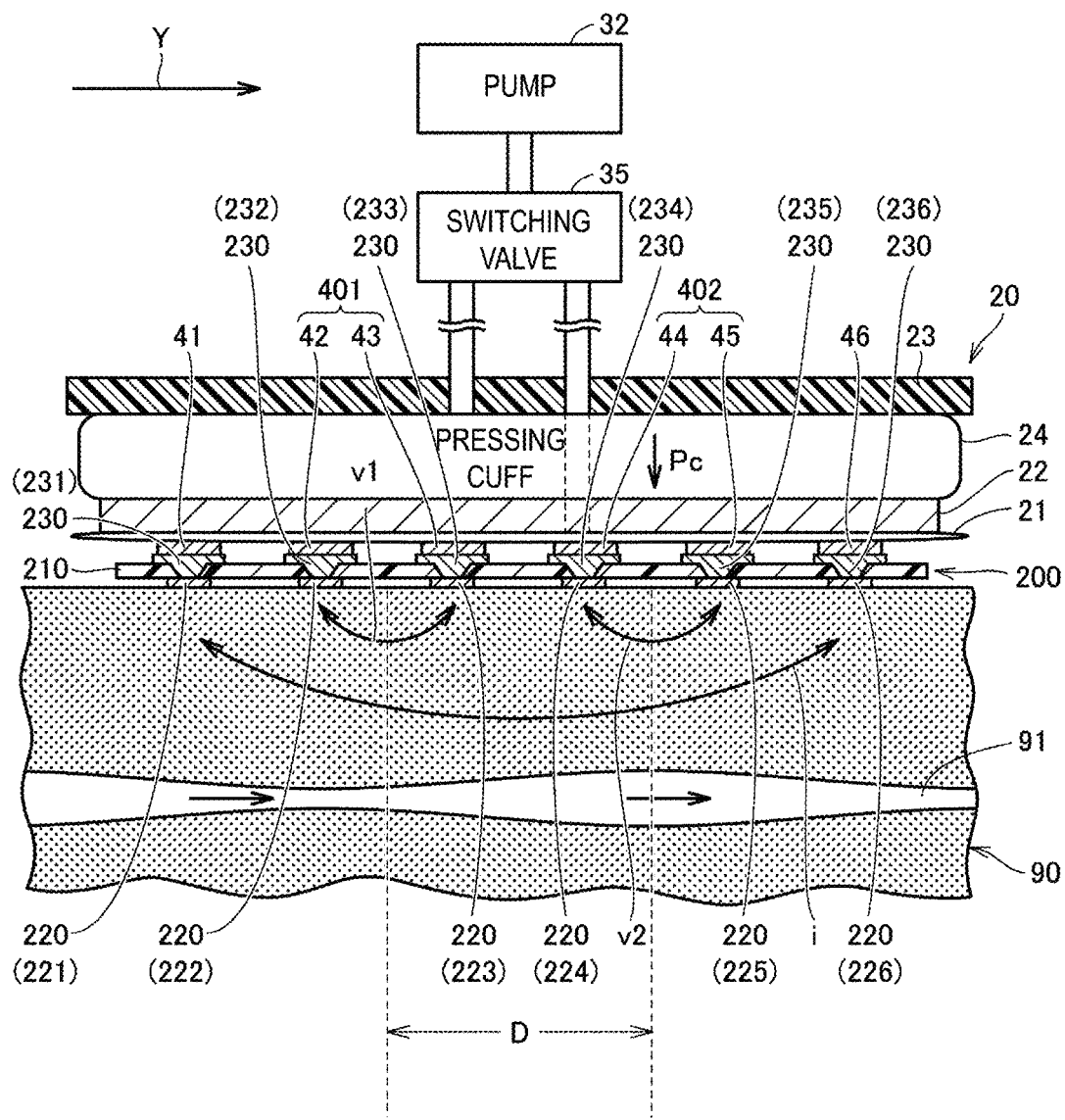
FIG. 9A is a diagram schematically illustrating the pulse wave measurement device according to the first embodiment in a worn state in a cross-section along the longitudinal direction of the wrist as it is when blood pressure measurement is performed on the basis of pulse transit time.
Figure 9B:
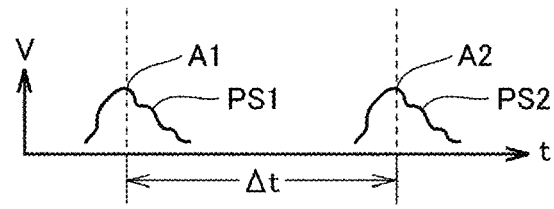
FIG. 9B is a diagram illustrating a first pulse wave signal waveform and a second pulse wave signal waveform output by a first pulse wave sensor and a second pulse wave sensor respectively in blood pressure measurement performed in the state illustrated in FIG. 9A.

FIG. 9A is a diagram schematically illustrating the pulse wave measurement device according to the first embodiment in a worn state in a cross-section along the longitudinal direction of the wrist as it is when blood pressure measurement is performed on the basis of pulse transit time. FIG. 9B is a diagram illustrating a first pulse wave signal waveform and a second pulse wave signal waveform output by the first pulse wave sensor and the second pulse wave sensor respectively in blood pressure measurement performed in the state illustrated in FIG. 9A.

The current flow and voltage detection circuit 49 of the impedance measurement portion 40 is controlled by the CPU 60. As illustrated in FIG. 9A, when the device is operating, the CPU 60 runs a high frequency constant current i between the electrodes 41, 46, i.e., the pair of current applying electrodes, disposed on either side in the longitudinal direction of the wrist (the width direction Y of the belt 20). For example, the high frequency constant current i is a current with a frequency of 50 kHz and a current value of 1 mA.

The electrodes 41, 46 come into contact with connection electrodes 231, 236 located on either end of the electrode unit 200 and are electrically connected to the measurement electrodes 221, 226 located on either end of the electrode unit 200 via the connection electrodes 231, 236.

Also, the electrodes 42, 43 that constitute the first pulse wave sensor 401 come into contact with the connection electrodes 232, 233 corresponding to the electrodes 42, 43 and are electrically connected to the measurement electrodes 222, 223 corresponding to the connection electrodes 232, 233 via the connection electrodes 232, 233.

Furthermore, the electrodes 44, 45 that constitute the second pulse wave sensor 402 come into contact with the connection electrodes 234, 235 corresponding to the electrodes 44, 45 and are electrically connected to the measurement electrodes 224, 225 corresponding to the connection electrodes 234, 235 via the connection electrodes 234, 235.

In a state in which the high frequency constant current i runs through the electrodes 41, 46 and between the measurement electrodes 221, 226 corresponding thereto, the current flow and voltage detection circuit 49 detects via the first pulse wave sensor 401 and the second pulse wave sensor 402 a voltage signal v1 between the measurement electrodes 222, 223 and a voltage signal v2 between the measurement electrodes 224, 225.

The voltage signals v1, v2 represent a change in electrical impedance caused by a pulse wave of the blood flow of the radial artery 91 at the portions corresponding to measurement electrodes 222 to 225 on the palm side surface 90a of the left wrist 90 (impedance method). The current flow and voltage detection circuit 49 rectifies, amplifies, and filters the voltage signals v1, v2 and outputs a first pulse wave signal PS1 and a second pulse wave signal PS2 having a mountain-shaped waveform as illustrated in FIG. 9B as time series. In the present embodiment, the voltage signals v1, v2 are approximately 1 mV. Also, peaks A1, A2 of the first pulse wave signal PS1 and the second pulse wave signal PS2 are 1 V, for example.

Note that in the case where the pulse wave velocity (PWV) of the blood flow of the radial artery 91 ranges from 100 cm/s to 2000 cm/s, a time difference $\Delta t$ between the first pulse wave signal PS1 and the second pulse wave signal PS2 ranges from 1.0 ms to 2.0 ms, where an actual interval D1 between the first pulse wave sensor 401 and the second pulse wave sensor 402 is 20 mm.

As illustrated in FIG. 9A, the pressing cuff 24 is in a pressurized state, and the compression cuff 21 is in a non-pressurized state with air being discharged from inside the compression cuff 21. The pressing cuff 24 is disposed, with respect to the artery direction of the radial artery 91, across the first pulse wave sensor 401, the second pulse wave sensor 402, and the electrodes 41, 46. Also, the solid material 22 is disposed, with respect to the artery direction of the radial artery 91, across the first pulse wave sensor 401, the second pulse wave sensor 402, and the electrodes 41, 46.

As such, when the pressing cuff 24 is pressurized by the pump 32, the first pulse wave sensor 401, the second pulse wave sensor 402, and the electrodes 41, 46 are pressed against the palm side surface 90a of the left wrist 90 by the solid material 22.

Thus, the electrodes 41 to 46 and the connection electrodes 231 to 236 can be brought into stable contact with one another, and the measurement electrodes 221 to 226 can be brought into stable contact with the left wrist. Note that the pressing force from the pressing cuff 24 can be set as appropriate.

In the present embodiment, the pressing cuff 24 is used as the pressing portion. This allows the pump 32 and the valve 33 to be used together with the compression cuff 21 and allows the configuration to be simplified. Also, the first pulse wave sensor 401, the second pulse wave sensor 402, and the electrodes 41, 46 can be pressed by the solid material 22. This allows the pressing force against the target measurement site to be even. As a result, blood pressure measurement based on pulse transit time can be performed with high precision.

Figure 10:
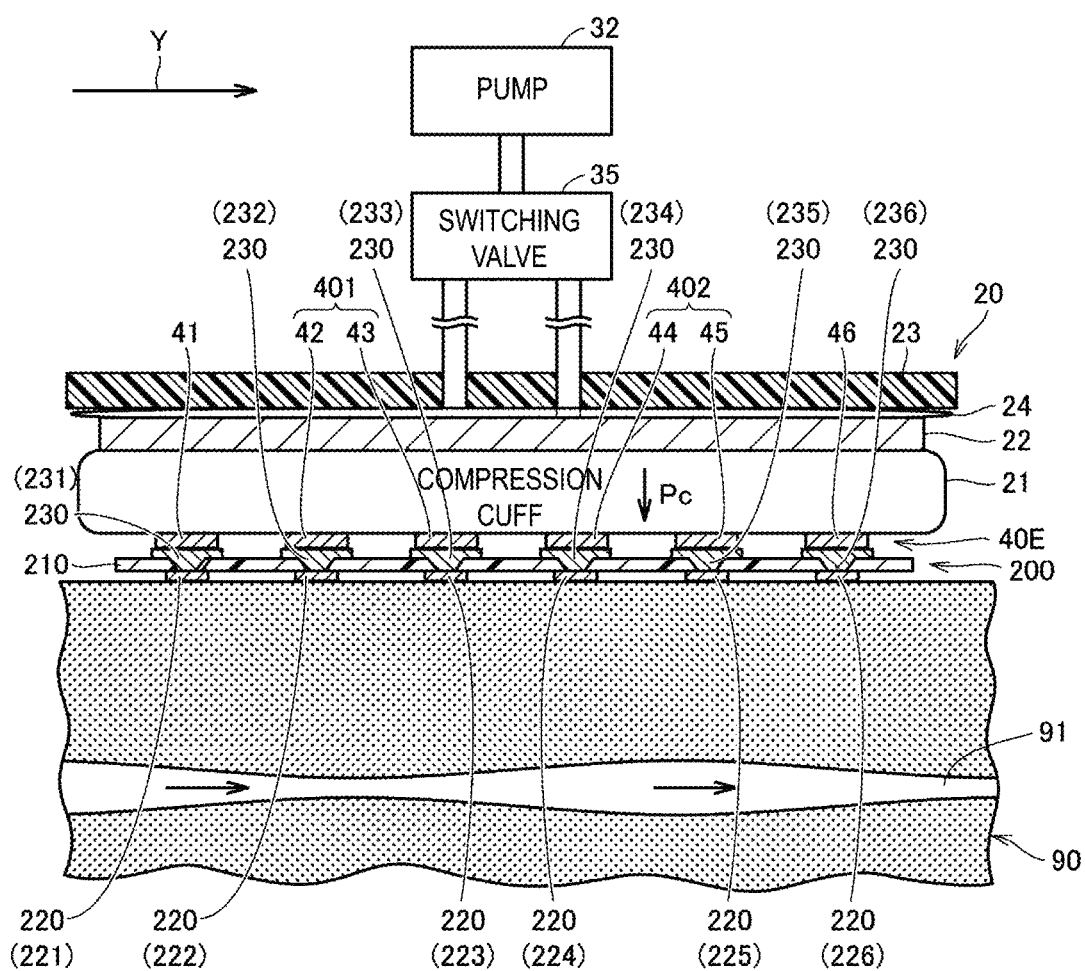
FIG. 10 is a diagram schematically illustrating the pulse wave measurement device according to the first embodiment in a worn state on the left wrist in a cross-section along the longitudinal direction of the wrist as it is when blood pressure measurement is performed via the oscillometric method.

FIG. 10 is a diagram schematically illustrating the pulse wave measurement device according to the first embodiment in a worn state of the left wrist in a cross-section along the longitudinal direction of the wrist as it is when blood pressure measurement is performed via the oscillometric method.

In this case, the pressing cuff 24 is in a non-pressurized state with air being discharged from inside the pressing cuff 24, and the compression cuff 21 is in a state of being supplied with air. The compression cuff 21 extends in the circumferential direction of the left wrist 90 and compresses the left wrist 90 uniformly with respect to the circumferential direction of the left wrist 90 when pressurized by the pump 32.

The electrode unit 200 and the electrodes 41 to 46 are located between the inner circumferential surface of the compression cuff 21 and the left wrist 90 and are flat and thin. Thus, the blood vessel can be sufficiently closed without other members hindering the compression by the compression cuff 21. Thus, blood pressure measurement via the oscillometric method can be performed with high precision.

Figure 11:
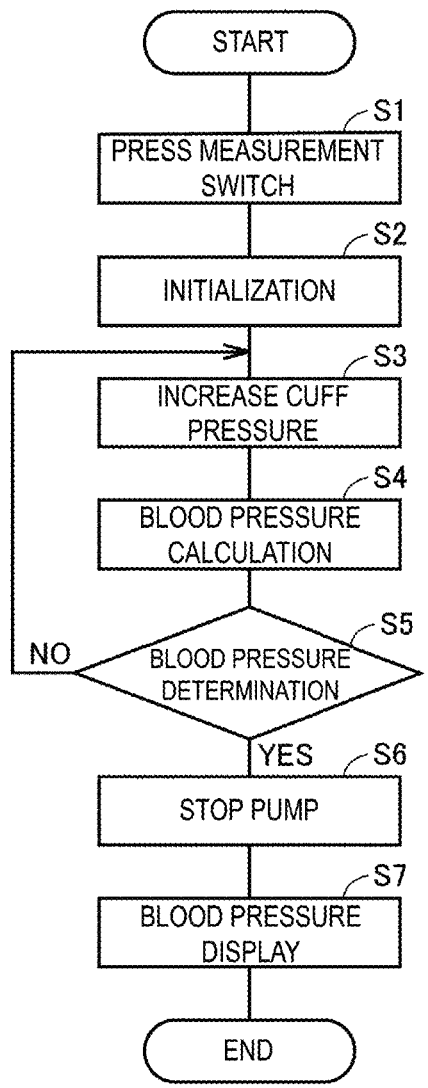
FIG. 11 is a diagram illustrating the operation flow of blood pressure measurement via the oscillometric method using the pulse wave measurement device according to the first embodiment.

FIG. 11 is a diagram illustrating the operation flow of blood pressure measurement via the oscillometric method using the pulse wave measurement device according to the first embodiment.

In the case where blood pressure measurement is performed via the oscillometric method, when the user sends an instruction for blood pressure measurement via the oscillometric method via the push type switch, i.e., the operation portion 52, provided on the body 10 (step S1), the CPU 60 starts operations and initializes a memory region for processing (step S2). The CPU 60 turns off the pump 32 via the pump drive circuit 320, opens the valve 33, and discharges the air in the compression cuff 21. Next, the output value of the first pressure sensor 31 at this time is set as a value corresponding to atmospheric pressure (adjusted to 0 mmHg).

Next, the CPU 60 closes the valve 33 and then drives the pump 32 via the pump drive circuit 320 to supply air to the compression cuff 21. This causes the compression cuff 21 to expand and the cuff pressure to gradually increase (step S3).

In the process of pressurizing, to calculate the blood pressure value, the CPU 60 monitors the cuff pressure via the first pressure sensor 31 and obtains, as a pulse wave signal, a variable component of the arterial volume generated in the radial artery 91 of the left wrist 90, i.e., the target measurement site.

Next, the CPU 60 functions as a second blood pressure calculation unit and attempts to calculate blood pressure values (of systolic blood pressure and diastolic blood pressure) on the basis of the obtained pulse wave signal at this point in time via the oscillometric method using a known algorithm.

At this point, if the blood pressure value cannot be calculated due to a lack of data (step S5: NO), unless the cuff pressure reaches an upper pressure limit, the processing of steps S3 to S5 are repeated. Note that the upper pressure limit is set in advance and may be 300 mmHg, for example.

If the blood pressure values can be calculated (step S5: YES), the CPU 60 stops the pump 32 via the pump drive circuit 320, opens the valve 33, and discharges the air in the compression cuff 21 (step S6). Lastly, the CPU 100 displays the blood pressure value measurement results on the display 50 and stores them in the memory 51 (step S7).

Note that the calculation of the blood pressure values is not limited being performed in the pressurizing process as described above and may be performed in the depressurizing process.

Figure 12:
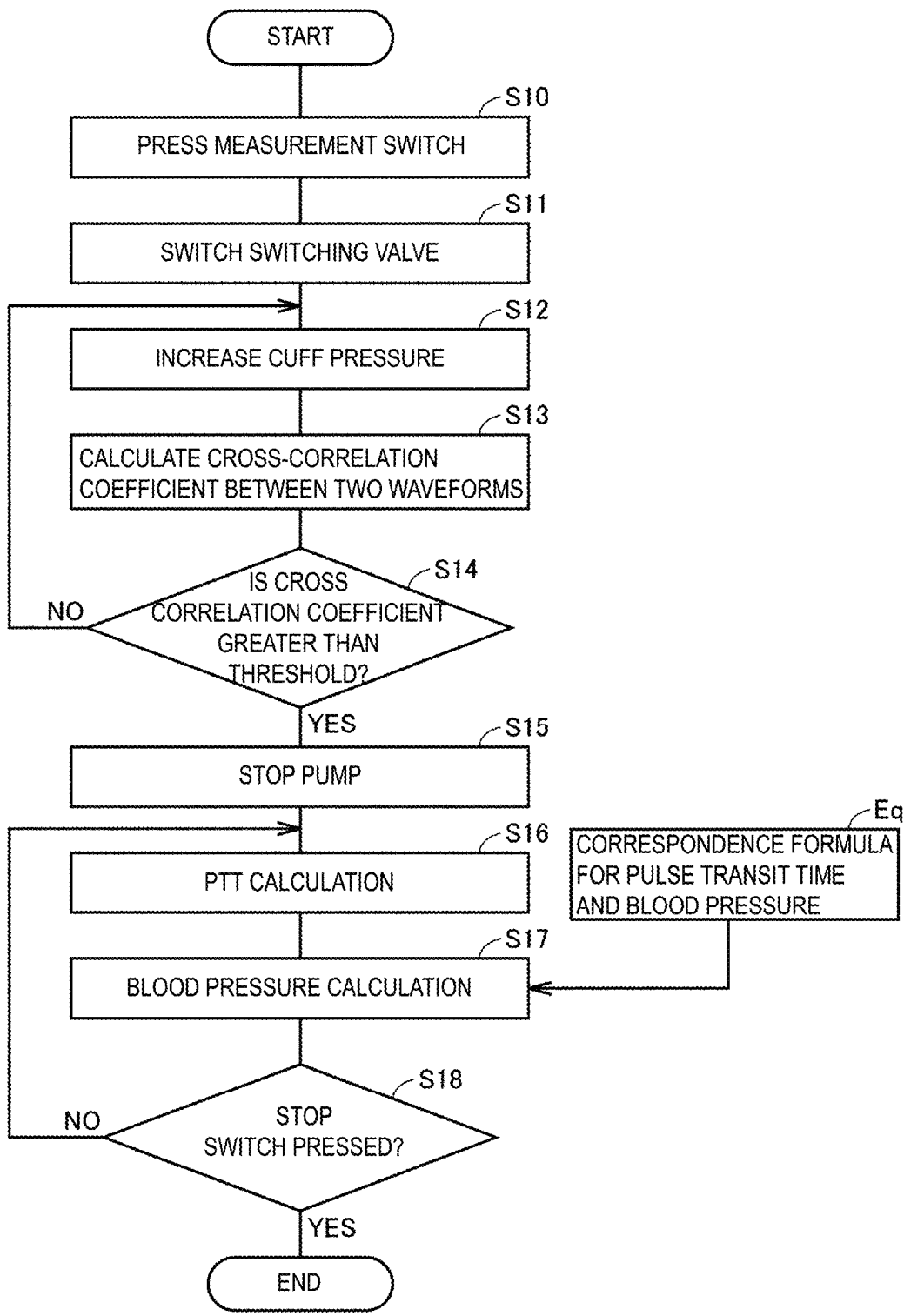
FIG. 12 is a diagram illustrating the operation flow of blood pressure measurement (estimation) on the basis of pulse transit time (PTT) using the pulse wave measurement device according to the first embodiment to obtain the pulse transit time.
Figure 13:
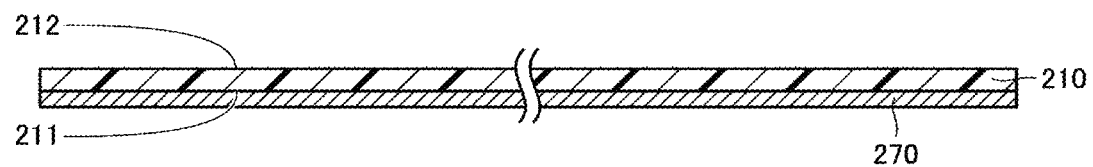
FIG. 13 is a cross-sectional view illustrating step 1 of a method of manufacturing the electrode unit according to the first embodiment.

FIG. 12 is a diagram illustrating the operation flow of blood pressure measurement (estimation) based on pulse transit time (PTT) using the pulse wave measurement device according to the first embodiment to obtain the pulse transit time.

As illustrated in FIG. 12, in the case where blood pressure measurement (estimation) is performed on the basis of pulse transit time, when the user sends an instruction for blood pressure measurement based on PTT via the push type switch, i.e., the operation portion 52, provided on the body 10 (step S10), the CPU 60 drives the switching valve 35 and switches the connection destination of the pump 32 and the valve 33 to the pressing cuff 24 (step S11). Next, the CPU 60 closes the valve 33 and drives the pump 32 via the pump drive circuit 320 to supply air to the pressing cuff 24. This causes the pressing cuff 24 to expand and the cuff pressure to gradually increase (step S12). For example, the cuff pressure is continuously increased at a constant speed by 5 mmHg/s. Note that the cuff pressure may be increased in steps to secure enough time to calculate a cross-correlation coefficient r described below.

In the pressurizing process, the CPU 60 functions a cross-correlation coefficient calculation unit, obtains the first pulse wave signal PS1 and the second pulse wave signal PS2 output as time series by the first pulse wave sensor 401 and the second pulse wave sensor 402, and calculates in real time the cross-correlation coefficient r between the waveforms of the first pulse wave signal PS1 and the second pulse wave signal PS2 (step S13).

Also, the CPU 60 functions as a pressing force setting unit and determines whether the calculated cross-correlation coefficient r is greater than a preset threshold Th (step S14). For example, the threshold Th is 0.99.

If the cross-correlation coefficient r is equal to or less than the threshold Th (step S14: NO), the processing of steps S12 to S14 is repeated until the cross-correlation coefficient r is greater than the threshold Th. If the cross-correlation coefficient r is greater than the threshold Th (step S14: YES), the CPU 60 stops the pump 32 (step S15) and sets the cuff pressure as the current value, i.e., the value at the point in time when the cross-correlation coefficient r became greater than the threshold Th.

In this state, the CPU 60 obtains the time difference Δt (see FIG. 9B) between the first pulse wave signal PS1 and the second pulse wave signal PS2 as a pulse transit time PTT (step S16). Specifically, the time difference Δt between the peak A1 of the first pulse wave signal PS1 and the peak A2 of the second pulse wave signal PS2 in FIG. 9B is determined to be the pulse transit time.

Obtaining the pulse transit time in this way can increase the measurement precision of the pulse transit time. Also, by setting the cuff pressure as the value at the point in time when the cross-correlation coefficient r became greater than the threshold Th, the pulse transit time can be obtained without needlessly increasing cuff pressure. This can reduce the physical burden on the user.

Next, the CPU 60 functions as a first blood pressure calculation unit and calculates (estimates) blood pressure on the basis of the pulse transit time obtained in step S16 using a preset correspondence formula for pulse transit time and blood pressure (step S17).

By blood pressure being calculated (estimated) in this way, the measurement precision of pulse transit time described above can be increased and blood pressure measurement precision can be increased. Note that the blood pressure value measurement results are displayed on the display 50 and stored in the memory 51.

In the present embodiment, in step S18, if a measurement stop instruction has not been received via the operation portion 52 (step S18: NO), calculation of pulse transit time (step S16) and calculation of blood pressure (step S17) are periodically repeated every time the first pulse wave signal PS1 and the second pulse wave signal PS2 corresponding to the pulse wave are input. The CPU 60 updates and displays the blood pressure value measurement results on the display 50 and cumulatively stores them in the memory 51. Then, if a measurement stop instruction has been received in step S18 (step S18: YES), measurement operation ends.

According to the pulse wave measurement unit 1, blood pressure can be continuously measured over an extended period of time on the basis of pulse transit time while keeping the physical burden on the user light.

Also, according to the pulse wave measurement unit 1, blood pressure measurement (estimation) based on pulse transit time and blood pressure measurement via the oscillometric method can be performed by one device. This can increase user convenience.

As described above, in the pulse wave measurement unit 1, the electrode unit 200 configured to be attached to a living body includes the substrate 210 with a sheet-like shape and insulating properties including the first main surface 211 and the second main surface 212, which are front and rear surfaces, the measurement electrodes 220 disposed on the first main surface 211, the connection electrodes 230 disposed on the second main surface 212, and the adhesive layer 240 configured to maintain the attached state of the electrode unit 200 being attached to the body surface of a living body. The connection electrodes 230 and the measurement electrodes 220 are electrically connected together in a 1-to-1 manner.

Also, the pulse wave measurement unit 1 including the pair of current applying electrodes and the pairs of voltage measuring electrodes and configured to be worn on a living body also includes a belt 20 configured to wrap around a living body and cover the electrode unit 200 in an attached state. The pair of current applying electrodes and the pairs of voltage measuring electrodes are disposed on the inner circumferential surface 20a of the belt 20 so that, when the belt 20 is in a wrapped state around a living body covering the electrode unit 200, each one of the pair of current applying electrodes and each one of the pairs of voltage measuring electrodes come into contact with any one of the connection electrodes.

The pulse wave measurement device 100 having such a configuration means that when the pulse wave measurement device 100 is worn on a living body, the electrode unit 200 is first attached to the body surface of the living body. Because the electrode unit 200 is formed flat, the electrode unit 200 can be easily attached to the body surface of a living body with the measurement electrodes 220 positioned above the artery. This allows the measurement electrodes 220 and the body surface of a living body to maintain good contact between one another and prevents the measurement electrodes 220 moving off a position above the artery.

When the electrode unit 200 is in an attached state, the connection electrodes 230 electrically connected in a 1-to-1 manner with the measurement electrodes 220 face outward. In this state, the belt 20 including the pair of current applying electrodes and the pairs of voltage measuring electrodes disposed on the inner circumferential surface 20a is wrapped around a living body starting from the outer side of the electrode unit 200.

Each one of the pair of current applying electrodes and each one of the pairs of voltage measuring electrodes are disposed in a manner allowing them to come into contact with any one of the connection electrodes 230. Thus, when the belt 20 is in a wrapped state, the pair of current applying electrodes and the pairs of voltage measuring electrodes are brought into stable contact with the connection electrodes 230. In this way, the measurement electrodes 220 that are positioned above the artery and come into contact with the body surface of a living body and the pair of current applying electrodes and the pairs of voltage measuring electrodes can be electrically connected via the connection electrodes 230 while corresponding to each other. As a result, by applying a voltage to flow a current between the pair of current applying electrode and using the pair of voltage measuring electrode, bioelectrical impedance can be measured with high precision.

As described above, by using the electrode unit 200, the pulse wave measurement unit 1, and the pulse wave measurement device 100 according to the first embodiment, the measurement precision of pulse wave measurement can be improved.

FIGS. 13 to 17 are cross-sectional views illustrating steps 1 to 5 of a method of manufacturing the electrode unit according to the first embodiment. The method of manufacturing the electrode unit 200 according to the first embodiment will be described with reference to FIGS. 13 to 17.

To manufacture the electrode unit 200, the substrate 210 with a metal layer 270 formed on the first main surface 211 side is prepared. The substrate 210 includes a sheet member with insulating properties. The metal layer 270 has a thickness ranging from a few μm to tens of μm. The metal layer 270 has high electrical conductivity and is made of a metal that is safe to use on the living body.

Figure 14:
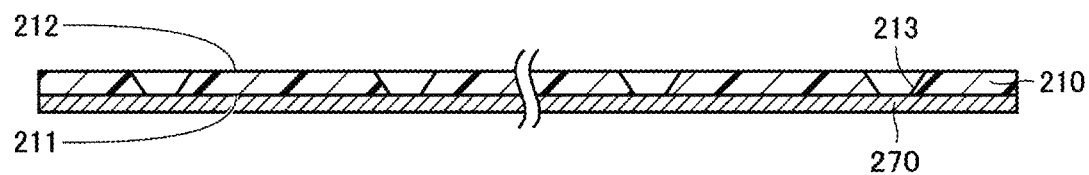
FIG. 14 is a cross-sectional view illustrating step 2 of a method of manufacturing the electrode unit according to the first embodiment.

Next, as illustrated in FIG. 14, through holes 213 are formed in the substrate 210 by irradiating the second main surface 212 of the substrate 210 with a laser beam. The through holes 213 extend through the substrate 210 but not through the metal layer 270. Note that the through holes 213 may be formed by a method other than laser beam irradiation.

Figure 15:
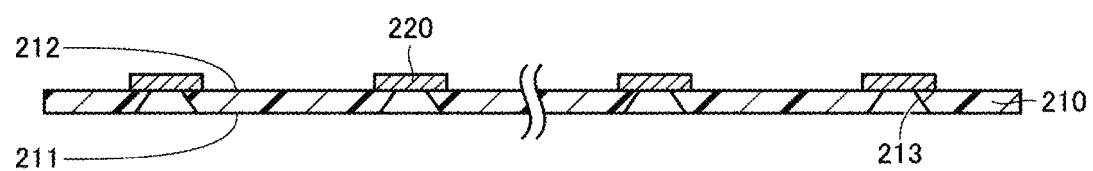
FIG. 15 is a cross-sectional view illustrating step 3 of a method of manufacturing the electrode unit according to the first embodiment.

Next, a resist pattern (not illustrated) corresponding to a desired measurement electrode pattern is printed on the first main surface 211 of the substrate 210 covering the metal layer 270 via a method such as screen printing, and etching is performed using the resist pattern as a mask. As illustrated in FIG. 15, as a result, the portion of the metal layer 270 not covered by the resist pattern is removed. Then, the resist pattern is removed. In this way, the measurement electrodes 220 are formed on the first main surface 211 of the substrate 210.

Figure 16:
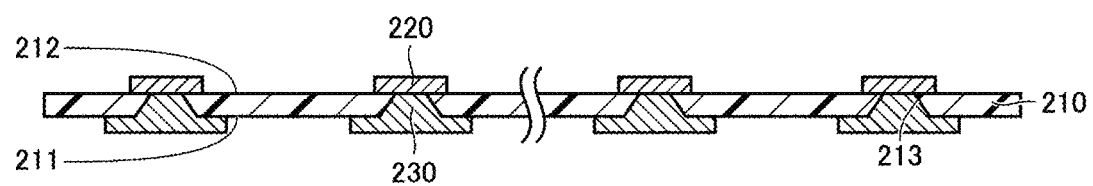
FIG. 16 is a cross-sectional view illustrating step 4 of a method of manufacturing the electrode unit according to the first embodiment.

Next, as illustrated in FIG. 16, the second main surface 212 of the substrate 210 is coated with a conductive paste by screen printing or the like, filling up the through holes 213. The conductive paste is then fired. In this way, the connection electrodes 230 are formed in the desired pattern.

Figure 17:
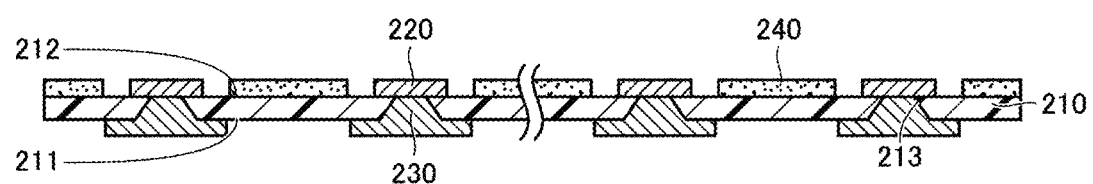
FIG. 17 is a cross-sectional view illustrating step 5 of a method of manufacturing the electrode unit according to the first embodiment.

Next, as illustrated in FIG. 17, the adhesive layer 240 is formed on the first main surface 211 of the substrate 210 with the measurement electrodes 220 exposed. For example, a thin film-like double-sided tape is attached on the first main surface 211. Via the steps described above, the electrode unit 200 according to the first embodiment is formed.

Second Embodiment

Figure 18:
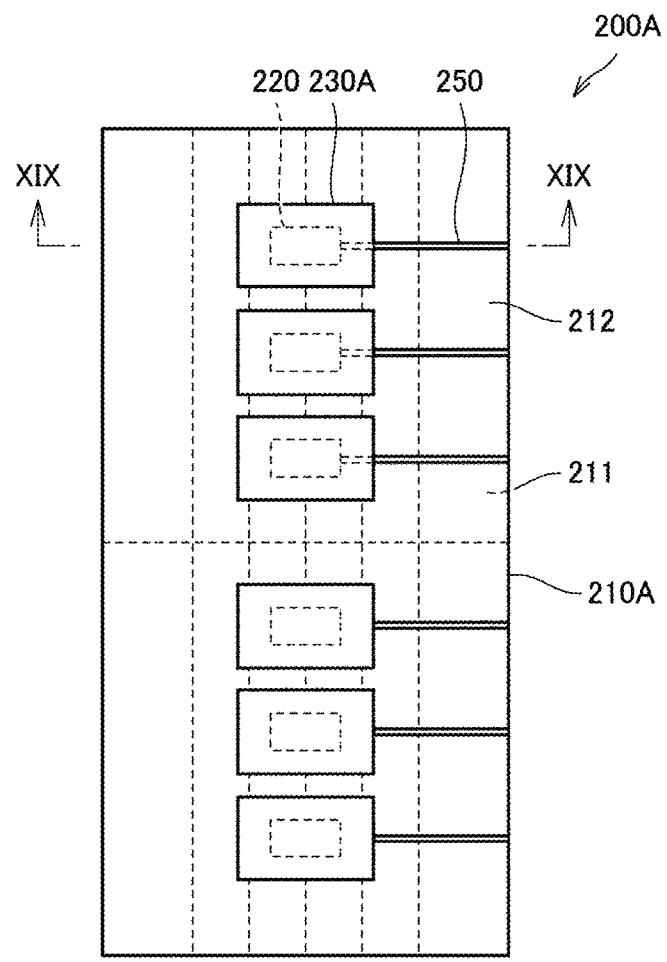
FIG. 18 is a plan view illustrating a second main surface side of an electrode unit according to a second embodiment.
Figure 19:
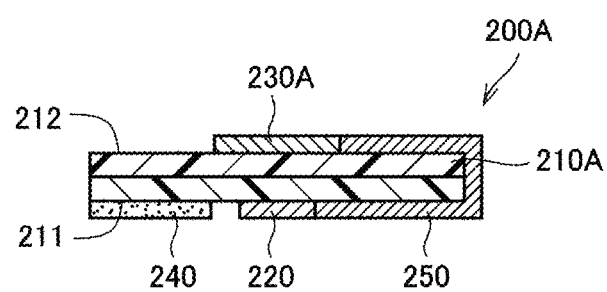
FIG. 19 is a cross-sectional view taken along line XIX-XIX illustrated in FIG. 18.

FIG. 18 is a plan view illustrating a second main surface side of an electrode unit according to a second embodiment. FIG. 19 is a cross-sectional view taken along line XIX-XIX illustrated in FIG. 18. An electrode unit 200A according to the second embodiment will be described with reference to FIGS. 18 and 19.

As illustrated in FIGS. 18 and 19, the electrode unit 200A according to the second embodiment is different from the electrode unit 200 according to the first embodiment in that the through holes 213 are not formed and wire portions 250 are further provided, the wire portions 250 connecting each one of the connection electrodes 230 and the corresponding one of the measurement electrodes 220. Other configurations are substantially similar.

Connection electrodes 230A are formed on the second main surface 212 of a substrate 210A. The measurement electrodes 220 are formed on the first main surface 211 of the substrate 210A. The wire portions 250 are disposed on the first main surface 211 and the second main surface 212 and connect a corresponding pair of the connection electrodes 230A and the measurement electrodes 220 while extending therebetween across a side surface of one end of the substrate 210A in the direction orthogonal to the direction in which the corresponding pair of the connection electrodes 230A and the measurement electrodes 220 overlap and orthogonal to the direction in which the measurement electrodes 220 are arranged.

The substrate 210A is formed by folding a single sheet member 260 (see FIG. 20) with insulating properties. Specifically, the substrate 210A is formed by folding the sheet member 260 so that a rear surface 260b (see FIG. 20) faces itself.

With such a configuration, the electrode unit 200A according to the second embodiment can obtain effects similar to that of the electrode unit 200 according to the first embodiment.

Figure 20:
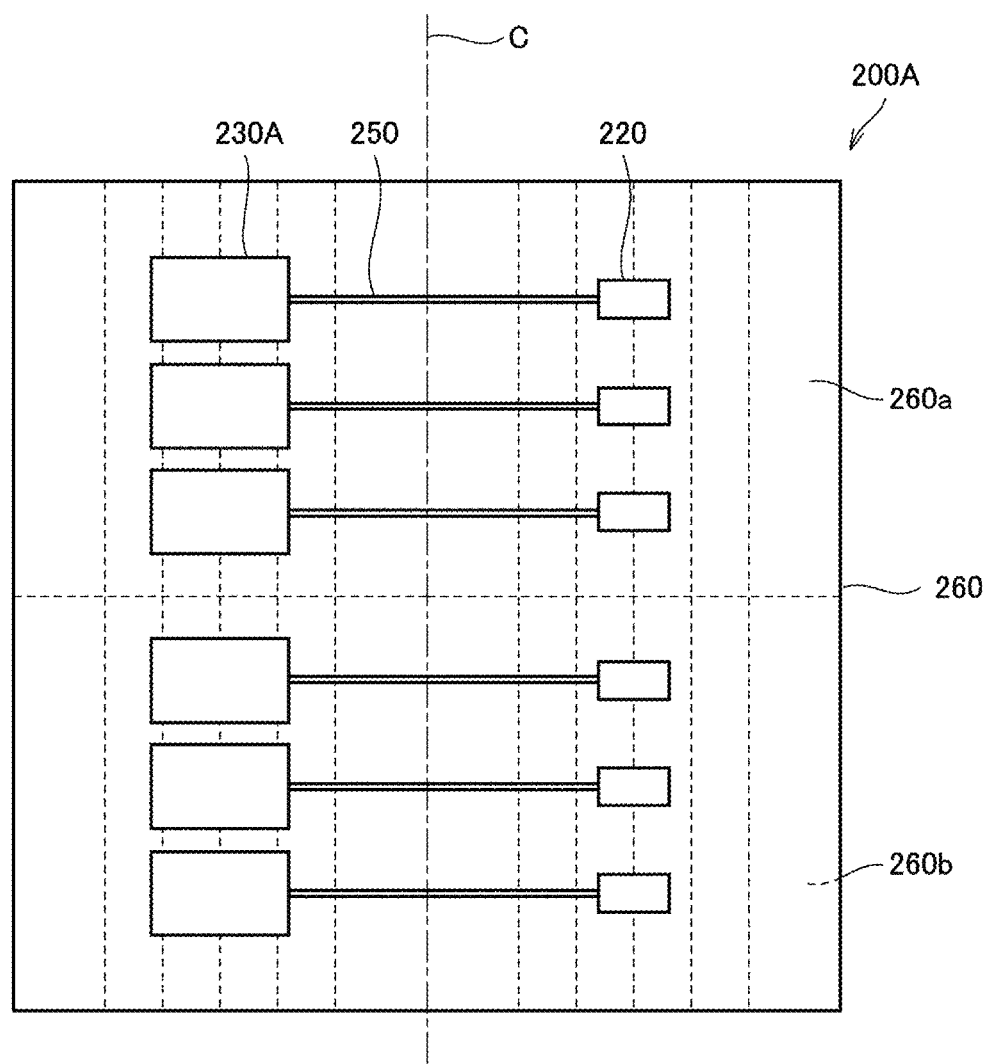
FIG. 20 is an unfolded view illustrating an electrode unit according to the second embodiment.

FIG. 20 is an unfolded view illustrating the electrode unit according to the second embodiment. A method of manufacturing the electrode unit 200A according to the second embodiment will be described with reference to FIG. 20.

As illustrated in FIG. 20, to manufacture the electrode unit 200A, first a front surface 260a and the rear surface 260b are defined, and on the front surface 260a, the measurement electrodes 220, the connection electrodes 230A, and the wire portions 250 are patterned (formed) to prepare the sheet member 260 with insulating properties. The measurement electrodes 220, the connection electrodes 230A, and the wire portions 250 are preferably integrally formed as a single member via screen printing, sputtering, or other such methods.

Next, the sheet member 260 is folded along a fold line C so that the rear surface 260b of the sheet member 260 faces itself. The fold line C, before the sheet member 260 is folded, is located between a corresponding pair of the connection electrodes 230A and the measurement electrodes 220 and extends in a direction parallel with the direction in which the measurement electrodes 220 are arranged.

The sheet member 260 is folded and the rear surface 260b is bonded to itself via an adhesive to form the substrate 210. The front surface 260a of the sheet member 260 on the side where the measurement electrodes 220 are formed corresponds to the first main surface 211 of the substrate 210, and the front surface 260a of the sheet member 260 on the side where the connection electrodes 230A are formed corresponds to the second main surface 212 of the substrate 210.

Next, the adhesive layer 240 is formed on the first main surface 211 of the substrate 210 with the measurement electrodes 220 and the wire portions 250 exposed. Via the steps described above, the electrode unit 200A according to the second embodiment is formed.

Note that the step of forming the adhesive layer 240 may be included in the step of preparing the sheet member 260. In this case, the sheet member 260 prepared may have the adhesive layer 240 formed on the sheet member 260 in advance along with the measurement electrodes 220, the connection electrodes 230A, and the wire portions 250. Also, the adhesive layer 240 may be formed before folding the sheet member 260. Furthermore, the wire portions 250 may be covered by a protective layer.

Third Embodiment

Figure 21:
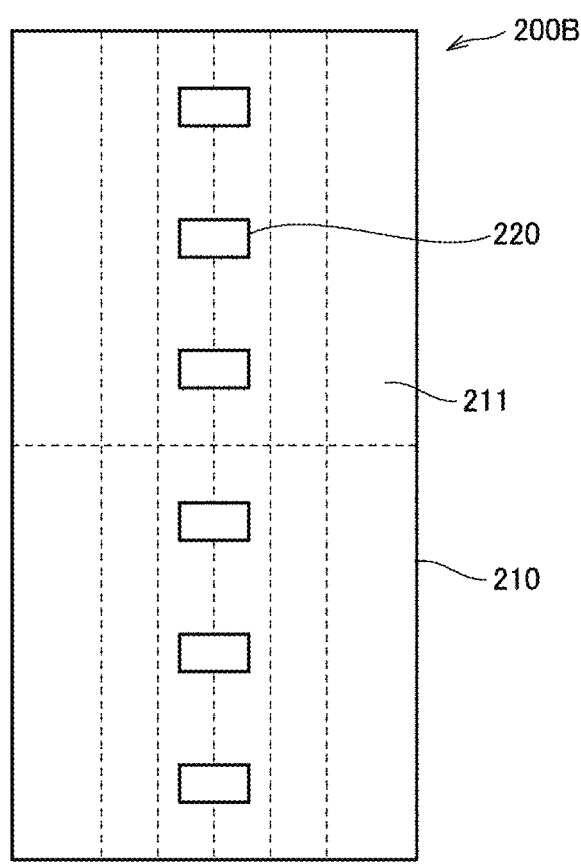
FIG. 21 is a plan view illustrating a first main surface side of an electrode unit according to a third embodiment.
Figure 22:
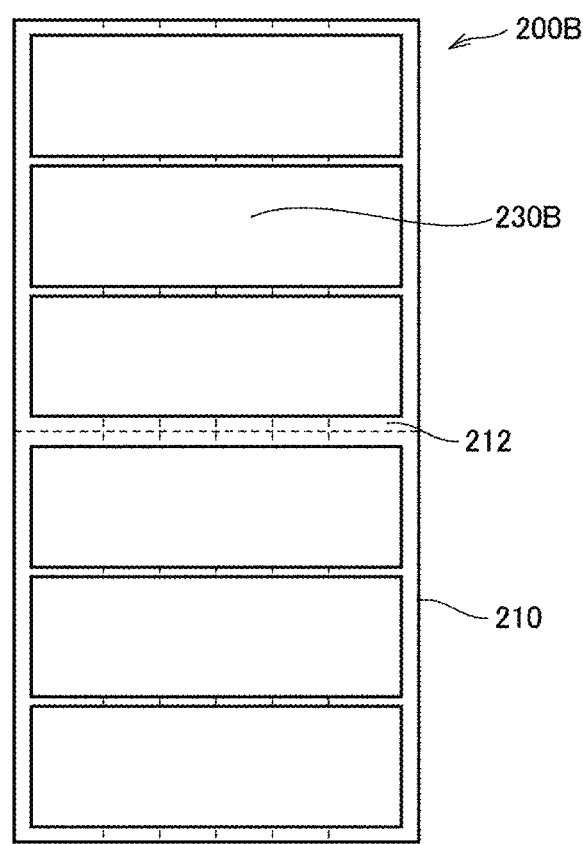
FIG. 22 is a plan view illustrating a second main surface side of the electrode unit according to the third embodiment.

FIG. 21 is a plan view illustrating a first main surface side of an electrode unit according to a third embodiment. FIG. 22 is a plan view illustrating a second main surface side of the electrode unit according to the third embodiment. An electrode unit 200B according to the third embodiment will be described with reference to FIGS. 21 and 22.

As illustrated in FIGS. 21 and 22, the electrode unit 200B according to the third embodiment is different from the electrode unit 200 of the first embodiment in that the size of connection electrodes 230B is different. Other configurations are substantially similar.

The connection electrodes 230B are slightly smaller than the substrate 210 in the direction orthogonal to the direction in which the first main surface 211 and the second main surface 212 overlap (thickness direction of the substrate 210) and orthogonal to the direction in which the measurement electrodes 220 are arranged.

Figure 23:
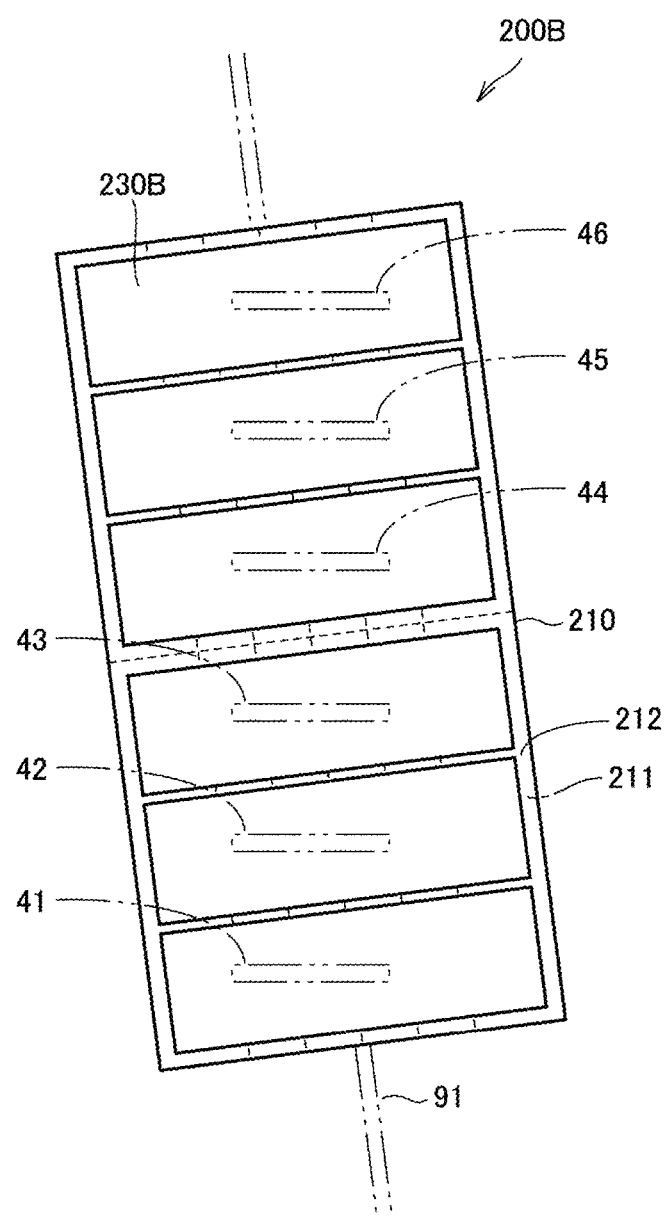
FIG. 23 is a plan view illustrating the positional relationship between the radial artery, measurement electrodes and connection electrodes of the electrode unit, and electrodes of a pulse wave measurement unit, when a pulse wave measurement device according to the third embodiment is worn on the left wrist.

FIG. 23 is a plan view illustrating the positional relationship between the radial artery, the measurement electrodes and the connection electrodes of the electrode unit, and the electrodes of the pulse wave measurement unit, when the pulse wave measurement device according to the third embodiment is worn on the left wrist. Note that FIG. 23 is a plan view of the second main surface 212 side of the electrode unit 200B in an attached state. The radial artery 91 and the electrodes 41 to 46 overlap one another in the plan view and are illustrated with a two-dot chain line.

As illustrated in FIG. 23, with the electrode unit 200B attached to the left wrist, the belt 20 is wrapped around the left wrist so that each of the electrodes 41 to 46 comes into contact with any one of the connection electrodes 230B. In this state, in a plan view of the substrate 210, each of the electrodes 41 to 46 is located within the connection electrode 230B.

That is, the width of the electrodes 41 to 46 in the width direction of the belt 20 is less than the width of the connection electrodes 230B in the width direction. The length of the electrodes 41 to 46 in the length direction of the belt 20 is less than the length of the connection electrodes 230B in the length direction.

With such a configuration, the electrode unit 200B according to the third embodiment can obtain effects similar to that of the electrode unit 200 according to the first embodiment.

Also, in a pulse wave measurement device including the electrode unit 200B according to the third embodiment, the electrodes 41 to 46 and the connection electrodes 230B have a size relationship described above. Thus, the electrodes 41 to 46 and the connection electrodes 230B can be easily positioned when the belt 20 is wrapped around the left wrist. This allows the pulse wave measurement unit 1 to be easily worn on a living body.

Note that the electrode unit 200B according to the third embodiment is manufactured basically according to the manufacturing method according to the first embodiment.

Fourth Embodiment

Figure 24:
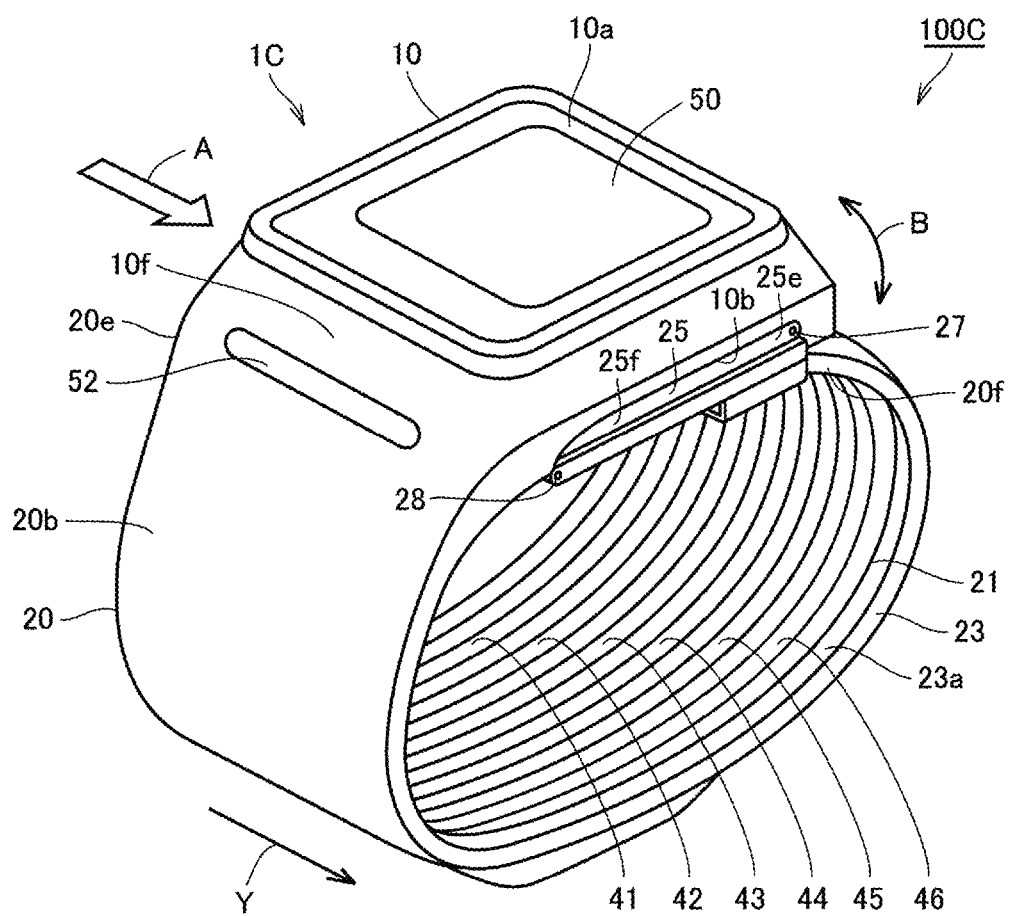
FIG. 24 is a perspective view illustrating a pulse wave measurement device according to a fourth embodiment.
Figure 24:
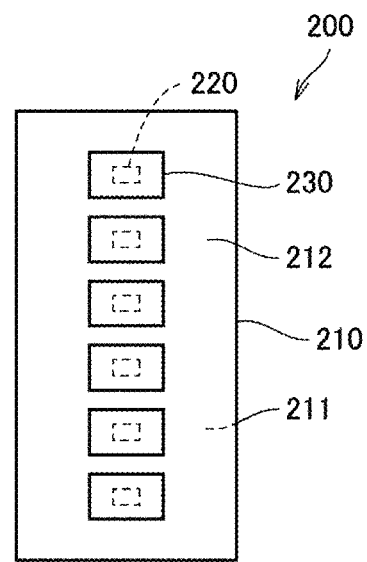

FIG. 24 is a perspective view illustrating a pulse wave measurement device according to a fourth embodiment. A pulse wave measurement device 100C according to the fourth embodiment will be described with reference to FIG. 24.

As illustrated in FIG. 24, the pulse wave measurement device 100C according to the fourth embodiment is different from the pulse wave measurement device 100 according to the first embodiment in that the configuration of a pulse wave measurement unit 1C is different. Other configurations are substantially similar.

The pulse wave measurement unit 1C according to the fourth embodiment is different from the pulse wave measurement unit 1 according to the first embodiment in that the shape of the electrodes 41 to 46 is different. Other configurations are substantially similar.

The electrodes 41 to 46 including the electrodes 41, 46, i.e., the pair of current applying electrodes, and the electrodes 42, 43, i.e., the pair of voltage measuring electrodes, are disposed extending from one end of the belt 20 to the other end in the length direction of the belt 20.

With such a configuration, the pulse wave measurement device 100C according to the fourth embodiment can obtain effects similar to that of the pulse wave measurement device 100 according to the first embodiment.

Also, the electrodes 41 to 46 being disposed extending from one end of the belt 20 to the other end removes the need for positioning in the circumferential direction when the belt 20 is wrapped around so that the electrodes 41 to 46 come into contact with the connection electrodes 230 of the attached electrode unit 200. This allows the electrodes 41 to 46 and the corresponding connection electrodes 230 to be easily aligned.

Fifth Embodiment

Figure 25:
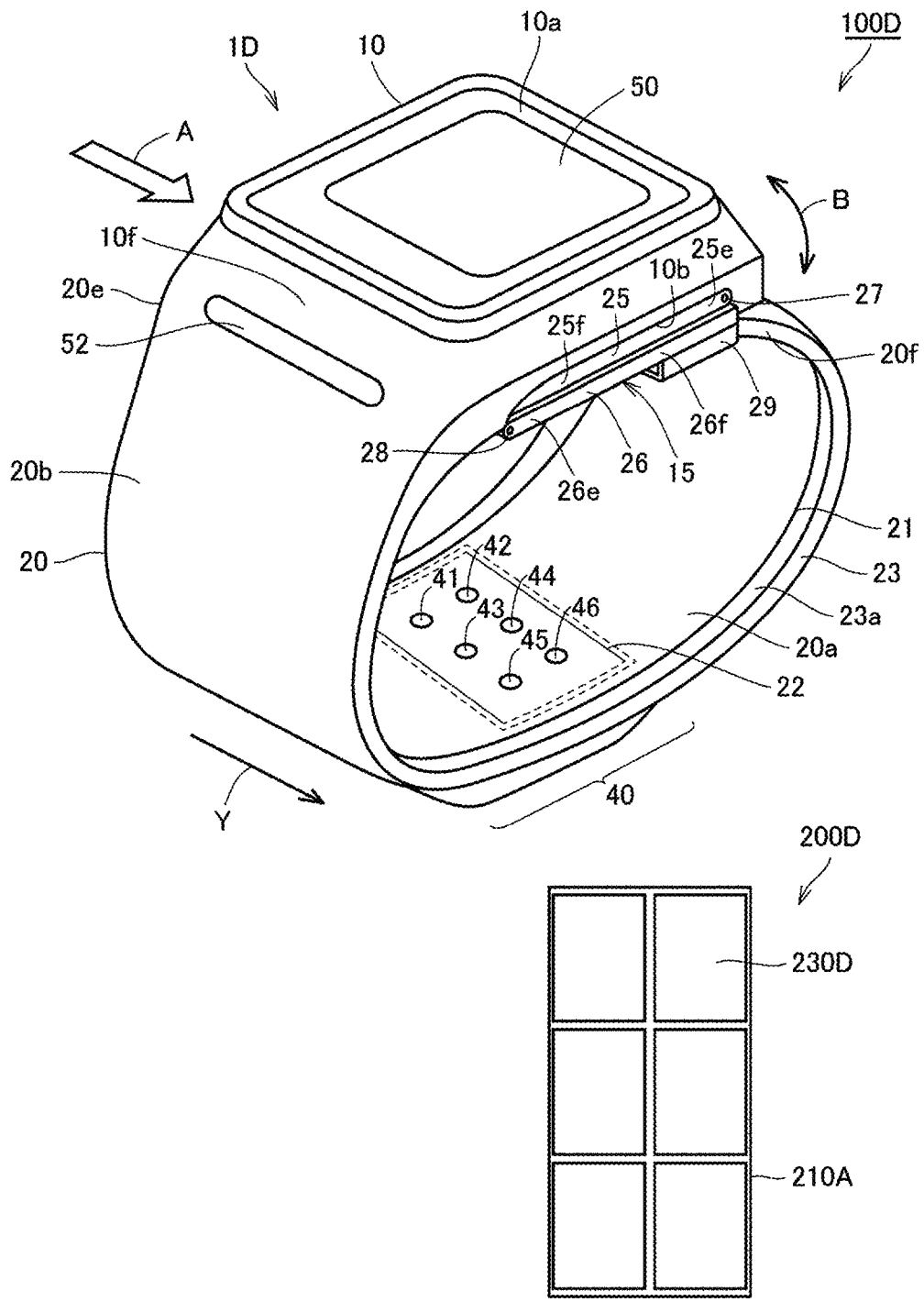
FIG. 25 is a perspective view illustrating a pulse wave measurement device according to a fifth embodiment.

FIG. 25 is a perspective view illustrating a pulse wave measurement device according to a fifth embodiment. A pulse wave measurement device 100D according to the fifth embodiment will be described with reference to FIG. 25.

As illustrated in FIG. 25, the pulse wave measurement device 100D according to the fifth embodiment is different from the pulse wave measurement device 100 according to the first embodiment in that the configuration of a pulse wave measurement unit 1D and the configuration of an electrode unit 200D are different. Other configurations are substantially similar.

The pulse wave measurement unit 1D according to the fifth embodiment is different from the pulse wave measurement unit 1 according to the first embodiment in that the position of the electrodes 41 to 46 is different. Other configurations are substantially similar.

The electrodes 41 to 46 are arranged in a matrix-like manner. Specifically, the electrodes 41 to 46 are arranged in two rows of three columns.

The electrodes 41, 42 are arranged side by side in the length direction of the belt 20. The electrodes 43, 44 are arranged side by side in the length direction of the belt 20. The electrodes 45, 46 are arranged side by side in the length direction of the belt 20.

The electrodes 41, 43, 45 are arranged side by side in the width direction of the belt 20. The electrodes 42, 44, 46 are arranged side by side in the width direction of the belt 20.

Figure 26:
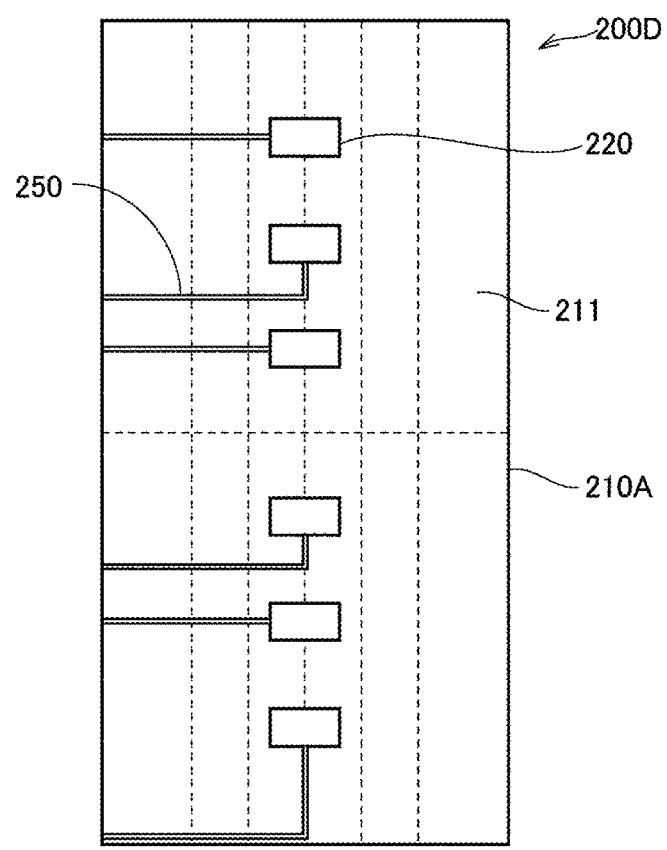
FIG. 26 is a plan view illustrating a first main surface side of an electrode unit according to the fifth embodiment.
Figure 27:
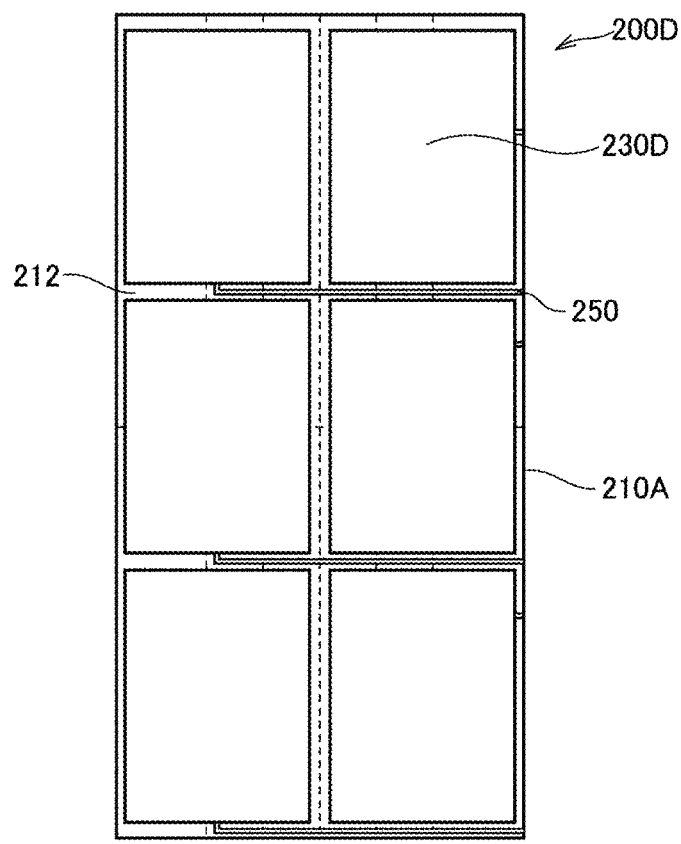
FIG. 27 is a plan view illustrating a second main surface side of an electrode unit according to the fifth embodiment.

FIG. 26 is a plan view illustrating a first main surface side of an electrode unit according to the fifth embodiment. FIG. 27 is a plan view illustrating a second main surface side of an electrode unit according to the fifth embodiment. The electrode unit 200D according to the fifth embodiment will be described with reference to FIGS. 26 and 27.

As illustrated in FIGS. 26 and 27, the electrode unit 200D according to the fifth embodiment is different from the electrode unit 200 according to the first embodiment in that the through holes 213 are not formed and wire portions 250 are further provided, the wire portions 250 connecting the connection electrodes 230D and the measurement electrodes 220. Other configurations are substantially similar.

The connection electrodes 230D are formed on the second main surface 212 of a substrate 210A. The connection electrodes 230D are arranged in a matrix-like manner. The connection electrodes 230D are formed slightly smaller than the size of each section of the substrate 210A divided into a matrix, the number of sections corresponding to the number of connection electrodes 230D.

The measurement electrodes 220 are formed on the first main surface 211 of the substrate 210A. The wire portions 250 are disposed on the first main surface 211 and the second main surface 212 and connect a corresponding pair of the connection electrodes 230D and the measurement electrodes 220 while extending therebetween across a side surface of one end of the substrate 210A in the direction orthogonal to the direction in which the corresponding pair of the connection electrodes 230D and the measurement electrodes 220 overlap and orthogonal to the direction in which the measurement electrodes 220 are arranged.

The substrate 210A is formed by folding a single sheet member 260 (see FIG. 29) with insulating properties. Specifically, the substrate 210A is formed by folding the sheet member 260 so that a rear surface 260b (see FIG. 29) faces itself.

Figure 28:
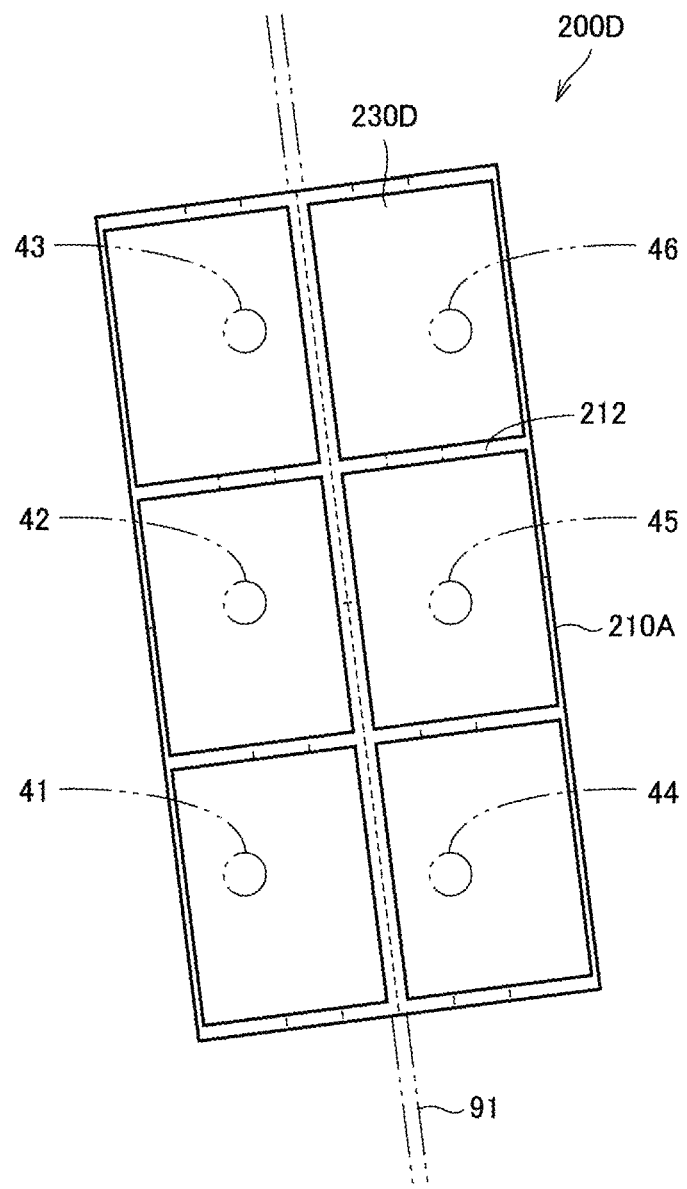
FIG. 28 is a plan view illustrating the positional relationship between the radial artery, measurement electrodes and connection electrodes of the electrode unit, and electrodes of a pulse wave measurement unit, when the pulse wave measurement device according to the fifth embodiment is worn on the left wrist.

FIG. 28 is a plan view illustrating the positional relationship between the radial artery, the measurement electrodes and the connection electrodes of the electrode unit, and the electrodes of the pulse wave measurement unit, when the pulse wave measurement device according to the fifth embodiment is worn on the left wrist. Note that FIG. 28 is a plan view of the second main surface 212 side of the electrode unit 200D in an attached state. The radial artery 91 and the electrodes 41 to 46 overlap one another in the plan view and are illustrated with a two-dot chain line.

As illustrated in FIG. 28, with the electrode unit 200D attached to the left wrist, the belt 20 is wrapped around the left wrist so that each of the electrodes 41 to 46 comes into contact with any one of the connection electrodes 230D. In this state, in a plan view of the substrate 210, each of the electrodes 41 to 46 is located within the connection electrode 230B, when viewed in the direction in which the first main surface 211 and the second main surface 212 of the substrate 210A overlap.

That is, the width of the electrodes 41 to 46 in the width direction of the belt 20 is less than the width of the connection electrodes 230D in the width direction. The length of the electrodes 41 to 46 in the length direction of the belt 20 is less than the length of the connection electrodes 230D in the length direction.

With such a configuration, the electrode unit 200D according to the fifth embodiment can obtain effects similar to that of the electrode unit 200 according to the first embodiment.

Also, in the pulse wave measurement device 100D including the electrode unit 200D according to the fifth embodiment, the electrodes 41 to 46 and the connection electrodes 230D have a size relationship described above. Thus, the electrodes 41 to 46 and the connection electrodes 230D can be easily positioned when the belt 20 is wrapped around the left wrist. This allows the pulse wave measurement unit 1D to be easily worn on a living body.

Figure 29:
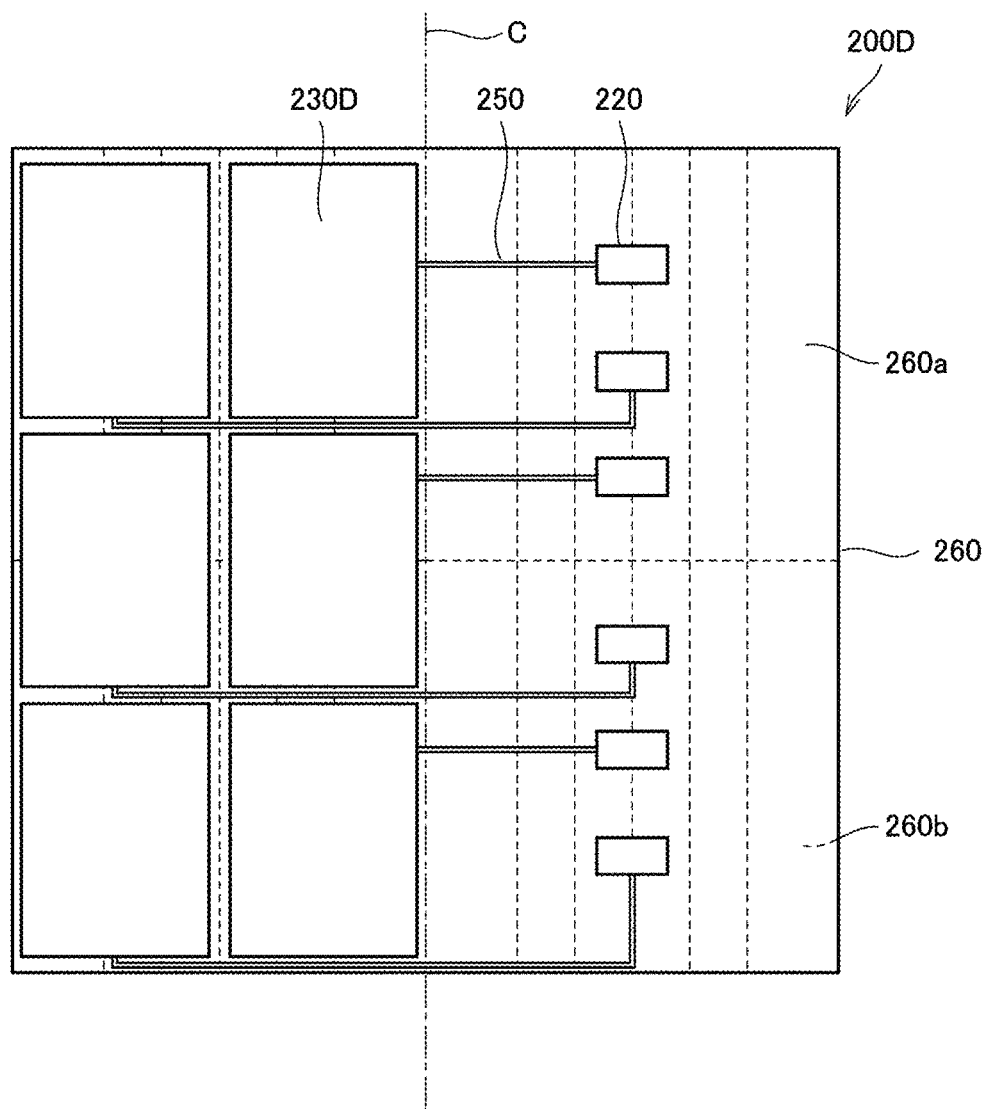
FIG. 29 is an unfolded view illustrating the electrode unit according to the fifth embodiment.

FIG. 29 is an unfolded view illustrating the electrode unit according to the fifth embodiment. A method of manufacturing the electrode unit 200D according to the fifth embodiment will be described with reference to FIG. 29.

As illustrated in FIG. 29, to manufacture the electrode unit 200D, first a front surface 260a and the rear surface 260b are defined, and on the front surface 260a, the measurement electrodes 220, the connection electrodes 230D, and the wire portions 250 are patterned to prepare the sheet member 260 with insulating properties.

Next, the sheet member 260 is folded along a fold line C so that the rear surface 260b of the sheet member 260 faces itself. The sheet member 260 is folded and the rear surface 260b is bonded to itself via an adhesive to form the substrate 210.

Next, the adhesive layer 240 is formed on the first main surface 211 of the substrate 210 with the measurement electrodes 220 and the wire portions 250 exposed. Via the steps described above, the electrode unit 200D according to the fifth embodiment is formed.

Note that the step of forming the adhesive layer 240 may be included in the step of preparing the sheet member 260. Also, the adhesive layer 240 may be formed before folding the sheet member 260. The wire portions 250 may be covered by a protective layer.

The configuration given as an example of the embodiment described above is an example configuration of the present invention. The configuration can be combined with other known technology, and parts thereof may be omitted or modified within the scope of the present invention.

An embodiment in which the pulse wave measurement unit is a blood pressure monitor including a blood pressure measurement function is described above. However, no such limitation is intended, and the pulse wave measurement unit may be a blood pressure estimation device configured to estimate a blood pressure. In this case, the pulse wave measurement unit may not include a compression cuff nor may it include a pressing cuff and a solid material. In the case where the compression cuff and the pressing cuff are not provided, a pressure sensor, a pump, a pump drive circuit, an air line, a switching valve, and the like may also not be provided, simplifying the configuration of the pulse wave measurement unit.

The embodiments described herein are illustrative in all respects and are not intended as limitations. The scope of the present invention is indicated by the claims and includes all meaning equivalent to the scope and changes within the scope.

REFERENCE SIGNS LIST 1, 1C, 1D Pulse wave measurement unit
10 Body
10b Bottom surface
15 Buckle
20 Belt
20a Inner circumferential surface
20b Outer circumferential surface
20e, 20f End portion
21 Compression cuff
21a Outer circumferential surface
22 Solid material
23 Band
23a Inner circumferential surface
24 Pressing cuff
25 First plate-like member
25e, 25f End portion
26 Second plate-like member
26e, 26f End portion
27, 28 Connecting rod
29 Fixing portion
31 First pressure sensor
32 Pump
33 Valve
34 Second pressure sensor
35 Switching valve
38a, 38b, 39a, 39b Air line
40 Impedance measurement portion
41, 42, 43, 44, 45, 46 Electrode
49 Current flow and voltage detection circuit
50 Display
51 Memory
52 Operation portion
53 Battery
59 Communication unit
71, 72 Wire
90 Left wrist
90a Palm side surface
91 Radial artery
100, 100C, 100D Pulse wave measurement device
200, 200A, 200B, 200C, 200D Electrode unit
210, 210A Substrate
211 First main surface
212 Second main surface 213 Through hole
220, 221, 222, 223, 224, 225, 226 Measurement electrode
230, 230A, 230B, 230C, 230D, 231, 232, 233, 234, 235, 236 Connection electrode
240 Adhesive layer
250 Wire portion
260 Sheet member
260a Front surface
260b Rear surface
270 Metal layer
310 Oscillation circuit
320 Pump drive circuit
340 Oscillation circuit
401 First pulse wave sensor
402 Second pulse wave sensor
900 Network

The invention claimed is:

1. A pulse wave measurement device configured to measure a volume pulse wave of an artery by measuring a change in bioelectrical impedance, the pulse wave measurement device comprising:
an electrode unit configured to be attached to a living body; and
a pulse wave measurement unit configured to be worn on the living body, the pulse wave measurement unit comprising a pair of current applying electrodes and a pair of voltage measuring electrodes, wherein
the electrode unit comprises
a substrate with a sheet shape and insulating properties, the substrate comprising a first main surface and a second main surface, which are opposing surfaces,
measurement electrodes disposed on the first main surface,
connection electrodes disposed on the second main surface and electrically connected in a 1-to-1 manner with the measurement electrodes, and
an adhesive layer configured to maintain an attached state of the electrode unit being attached to a body surface of the living body,
the pulse wave measurement unit further comprises
a belt member configured to wrap around the living body and cover the electrode unit in the attached state,
the belt member is configurable to be in a wrapped state of being wrapped around the living body covering the electrode unit with the pair of current applying electrodes and the pair of voltage measuring electrodes being disposed on an inner circumferential surface of the belt member, and with each one of the pair of current applying electrodes and each one of the pair of voltage measuring electrodes coming into contact with any one of the connection electrodes, and
the pulse wave measurement unit and the electrode unit are separate units that are not fastened to each other.

2. The pulse wave measurement device according to claim 1, wherein
the connection electrodes have a greater size than the measurement electrodes.

3. The pulse wave measurement device according to claim 1, wherein
the measurement electrodes are arranged side by side in a row, and
the connection electrodes are arranged side by side in a direction parallel to a direction in which the measurement electrodes are arranged.

4. The pulse wave measurement device according to claim 1, wherein
the connection electrodes and the measurement electrodes are arranged in electrically connected pairs at overlapping positions in a plan view of the substrate.

5. The pulse wave measurement device according to claim 1, wherein the connection electrodes are arranged in a matrix-shaped manner.

6. The pulse wave measurement device according to claim 1, wherein
the electrode unit further comprises wire portions that connect the connection electrodes to the measurement electrodes,
the substrate comprises a sheet member with insulating properties that comprises a front surface and a rear surface, the sheet member being folded with the rear surface facing itself; and
the measurement electrodes, the connection electrodes, and the wire portions are formed on the front surface, which includes the first main surface and the second main surface, of the sheet member with insulating properties.

7. The pulse wave measurement device according to claim 1, wherein
the belt member comprises a length direction corresponding to a circumferential direction of the belt member in the wrapped state and a width direction orthogonal to the length direction, and
a width of the pair of current applying electrodes and the pair of voltage measuring electrodes in the width direction is less than a width of the connection electrodes in the width direction.

8. The pulse wave measurement device according to claim 7, wherein
a length of the pair of current applying electrodes and the pair of voltage measuring electrodes in the length direction is less than a length of the connection electrodes in the length direction.

9. The pulse wave measurement device according to claim 8, wherein
the connection electrodes are arranged in a matrix-shaped manner, and
the pair of current applying electrodes and the pair of voltage measuring electrodes are arranged in a matrix-shaped manner.

10. The pulse wave measurement device according to claim 7, wherein
a length of the pair of current applying electrodes and the pair of voltage measuring electrodes in the length direction is greater than a length of the connection electrodes in the length direction.

11. A pulse wave measurement unit configured to be worn on a living body for measuring a volume pulse wave of an artery by measuring a change in bioelectrical impedance, the pulse wave measurement unit comprising:
a pair of current applying electrodes and a pair of voltage measuring electrodes; and
a belt member configured to wrap around the living body and cover an electrode unit in a state in which the electrode unit is attached to a body surface of the living body, the electrode unit being configured to be attached to the body surface of the living body and comprising measurement electrodes and connection electrodes disposed on front and rear surfaces of a sheet-shaped substrate with insulating properties and electrically connected in a 1-to-1 manner, wherein
the belt member is configurable to be in a wrapped state of being wrapped around the living body covering the electrode with the pair of current applying electrodes and the pair of voltage measuring electrodes being disposed on an inner circumferential surface of the belt member, and with each one of the pair of current applying electrodes and each one of the pair of voltage measuring electrodes coming into contact with any one of the connection electrodes, and the pulse wave measurement unit and the electrode unit are separate units that are not fastened to each other.

12. The pulse wave measurement unit according to claim 11, wherein the belt member comprises a length direction corresponding to a circumferential direction of the belt member in the wrapped state and a width direction orthogonal to the length direction, and the pair of current applying electrodes and the pair of voltage measuring electrodes are arranged side by side in the width direction.

13. The pulse wave measurement unit according to claim 12, wherein the pair of current applying electrodes and the pair of voltage measuring electrodes extend from one end of the belt member in the length direction to another end of the belt member.

14. The pulse wave measurement unit according to claim 11, wherein the pair of current applying electrodes and the pair of voltage measuring electrodes are arranged in a matrix-shaped manner.

* * * * *